(12) United States Patent
Kasperchik et al.

(10) Patent No.: US 11,602,502 B2
(45) Date of Patent: Mar. 14, 2023

(54) THREE-DIMENSIONAL (3D) PRINTING A PHARMACEUTICAL TABLET

(71) Applicant: Hewlett-Packard Development Company, L.P., Spring, TX (US)

(72) Inventors: Vladek Kasperchik, Corvallis, OR (US); Michael G. Monroe, Corvallis, OR (US); Michael J. Regan, Singapore (SG)

(73) Assignee: HEWLETT-PACKARD DEVELOPMENT COMPANY, L.P., Spring, TX (US)

( * ) Notice: Subject to any disclaimer, the term of this patent is extended or adjusted under 35 U.S.C. 154(b) by 430 days.

(21) Appl. No.: 16/466,975

(22) PCT Filed: Feb. 24, 2017

(86) PCT No.: PCT/US2017/019282
§ 371 (c)(1),
(2) Date: Jun. 5, 2019

(87) PCT Pub. No.: WO2018/156141
PCT Pub. Date: Aug. 30, 2018

(65) Prior Publication Data
US 2019/0343769 A1 Nov. 14, 2019

(51) Int. Cl.
*A61K 9/20* (2006.01)
*B33Y 70/00* (2020.01)
*B29C 64/165* (2017.01)
*A61K 47/32* (2006.01)
*A61K 47/38* (2006.01)
*B33Y 10/00* (2015.01)
*B33Y 80/00* (2015.01)

(52) U.S. Cl.
CPC .......... *A61K 9/2095* (2013.01); *A61K 9/2027* (2013.01); *A61K 47/32* (2013.01); *A61K 47/38* (2013.01); *B29C 64/165* (2017.08); *B33Y 70/00* (2014.12); *B33Y 10/00* (2014.12); *B33Y 80/00* (2014.12)

(58) Field of Classification Search
None
See application file for complete search history.

(56) References Cited

U.S. PATENT DOCUMENTS

| 9,463,160 B2 | 10/2016 | Yoo et al. |
| 2002/0106412 A1 | 8/2002 | Rowe et al. |
| 2003/0143268 A1 | 7/2003 | Pryce Lewis et al. |
| 2017/0297109 A1* | 10/2017 | Gibson ................. B29C 64/268 |

FOREIGN PATENT DOCUMENTS

| EP | 2532349 | 12/2012 |
| WO | WO-0187272 | 11/2001 |
| WO | WO-2013030726 | 3/2013 |
| WO | WO-2014144512 | 9/2014 |

OTHER PUBLICATIONS

Norman, J. et al.; A New Chapter in Pharmaceutical Manufacturing: 3d-printed Drug Products; Mar. 18, 2016.
Yu, DG et al.; Institute of Biological Sciences and Biotechnology, Donghua University; Three-dimensional Printing in Pharmaceutics: Promises and Problems; Sep. 2008.

* cited by examiner

*Primary Examiner* — Robert A Wax
*Assistant Examiner* — Randeep Singh
(74) *Attorney, Agent, or Firm* — Shook, Hardy & Bacon L.L.P.

(57) ABSTRACT

In an example of a three-dimensional (3D) printing method for forming a pharmaceutical tablet, build material granules are applied. Each of the build material granules includes a plurality of excipient particles, wherein at least one of the plurality of excipient particles is a latent binder. Pressure is applied to the build material granules. An activation solvent is selectively applied on at least a portion of the pressed build material granules. An active pharmaceutical ingredient formulation including an active pharmaceutical ingredient is selectively applied on the at least the portion of the pressed build material granules. The activation solvent is evaporated.

14 Claims, 7 Drawing Sheets

THREE-DIMENSIONAL (3D) PRINTING A PHARMACEUTICAL TABLET

BACKGROUND

Three-dimensional (3D) printing may be an additive printing process used to make three-dimensional solid parts from a digital model. 3D printing is often used in rapid product prototyping, mold generation, mold master generation, and short run manufacturing. Some 3D printing techniques are considered additive processes because they involve the application of successive layers of material. This is unlike traditional machining processes, which often rely upon the removal of material to create the final part. 3D printing often requires curing or fusing of the building material, which for some materials may be accomplished using heat-assisted extrusion, melting, or sintering, and for other materials may be accomplished using digital light projection technology.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1:
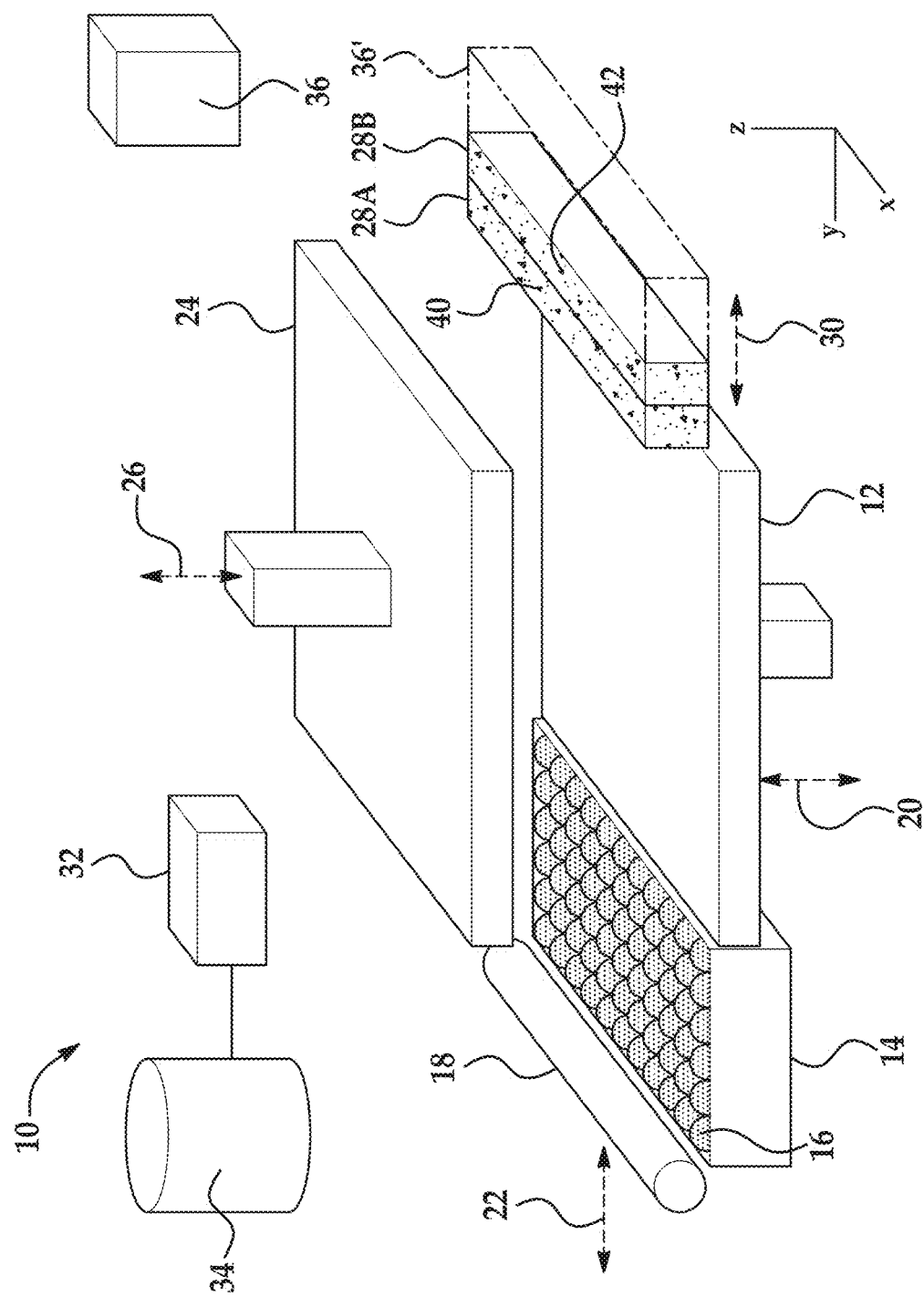
FIG. 1 is a simplified isometric view of an example 3D printing system disclosed.

Three-dimensional (3D) printing has been used to produce a variety of products, including pharmaceutical tablets. In some examples of the 3D printing of pharmaceutical tablets, a binder fluid (also known as a liquid functional agent/material) is selectively applied to a layer of loose excipient powder, and then another layer of the loose excipient powder is applied thereon. The binder fluid may be applied to this other layer of loose excipient powder, and these processes may be repeated to form the pharmaceutical tablet. The binder fluid may include an active pharmaceutical ingredient and a food-grade binder that holds the loose excipient powder together.

When loose excipient powder is used as a build material, the printed pharmaceutical tablet may have a rough surface. This rough surface may be undesirable, both texturally and ascetically, to consumers. Further, food-grade binders may cause the binder fluid to have a viscosity that is too high for application via inkjet printing (e.g., thermal inkjet printing or piezoelectric inkjet printing).

The example 3D printing method and system disclosed herein utilize a combination of build material granules (each of which includes a plurality of excipient particles, wherein at least one of the plurality of excipient particles is a latent binder), pressure application, an activation solvent, and an active pharmaceutical ingredient formulation (which includes an active pharmaceutical ingredient) in order to produce a pharmaceutical tablet in a dry cake of pressed and/or crushed build material granules. The presence of the latent binder in the build material granules eliminates the need for a highly viscous (often not inkjettable) binder fluid. Moreover, both the activation solvent and the active pharmaceutical ingredient formulation disclosed herein may be applied via inkjet printing. Inkjet printing enables control over the jetted flux of the activation solvent and the active pharmaceutical ingredient formulation. The use of inkjet printing, in combination with the pressure application, enables control over the structure (e.g., the internal distribution of the active pharmaceutical ingredient), the structural density, and the surface smoothness of the printed pharmaceutical tablets.

Each build material granule disclosed herein is composed of a plurality of excipient components (e.g., particles), at least one of which is a latent binder. The build material granules are large enough (e.g., >20 μm) to enable thin layers with well controlled uniformity to be formed during spreading of the build material granules. Granules of this size can flow easily and be spread in substantially uniform layers to receive the activation solvent and the active pharmaceutical ingredient formulation. Additionally, the latent binder of the build material granules is selected so that it is at least partially soluble in the activation solvent that is used during printing. Dissolution of the binder helps to break down the granular structure, enables agglomeration of the plurality of excipient particles, and enables higher structural uniformity of the pharmaceutical tablet that is formed upon evaporation of the activation solvent.

The application of pressure to the build material granules may tighten the packing of the build material granules or may crush the build material granules into smaller build material fragments. The amount of pressure applied (and thus, whether the build material granules are packed or crushed) may depend on the desired porosity and/or density of the pharmaceutical tablet. Tightly packing the build material granules may result in a highly porous, less dense pharmaceutical tablet (e.g., when compared to the tablet formed from crushed build material granules). Crushing the build material granules into smaller build material fragments may result in a less porous, highly dense pharmaceutical tablet. The smaller the build material fragments, the less porous and the denser the pharmaceutical tablet will be. Some of the granules may break down to the primary excipient particles. In this regard, primary excipient particles are in closer proximity to each other (than the granules), thereby increasing the packing density of the excipient particles within the layer of build material, which enables a less porous and denser pharmaceutical tablet. The porosity and/or density of the pharmaceutical tablet may affect the dissolution rate of the pharmaceutical tablet, and therefore, the release rate of the active pharmaceutical ingredient. A highly porous, less dense pharmaceutical tablet may result in a faster dissolution rate, and a less porous, highly dense pharmaceutical tablet may result in a slower dissolution rate.

In some examples, the application of pressure also eliminates macroscopic porosity that is present between the build material granules after spreading and before the pressure application, and produces a build material layer with predominantly microscopic porosity between the pressed and/or crushed build material granules. As such, pressure application replaces a smaller number of large diameter pores with a larger number of small diameter pores. Microscopic porosity facilitates uniform wetting and penetration of the activation solvent and the active pharmaceutical ingredient formulation throughout the pressed and/or crushed build material granules, in part because the lack of large diameter pores prevents non-controlled wicking of the activation solvent and active pharmaceutical ingredient formulation outside of the patterned build material granules or fragments.

As previously mentioned, the active pharmaceutical ingredient formulation includes the active pharmaceutical ingredient, which may be dissolved or dispersed in a liquid vehicle. During application of the active pharmaceutical ingredient formulation, the active pharmaceutical ingredient is capable of penetrating into the microscopic pores of the layer of pressed and/or crushed build material granules. As such, the active pharmaceutical ingredient can move into the vacant spaces between the pressed and/or crushed build material granules. Additionally, the active pharmaceutical ingredient may, upon dissolution of the latent binder in the activation solvent, become dissolved or dispersed in the dissolved latent binder phase. Thus, the active pharmaceutical ingredient may be at least substantially uniformly applied throughout the pharmaceutical tablet.

Referring now to FIG. 1, an example of a 3D printing system 10 is depicted. It is to be understood that the 3D printing system 10 may include additional components and that some of the components described herein may be removed and/or modified. Furthermore, components of the 3D printing system 10 depicted in FIG. 1 may not be drawn to scale and thus, the 3D printing system 10 may have a different size and/or configuration other than as shown therein.

The printing system 10 generally includes a supply 14 of build material granules 16, each of the build material granules 16 including a plurality of excipient particles and a latent binder; a build material distributor 18; a pressing die 24; a supply of an activation solvent 40; a first inkjet applicator 28A for selectively dispensing the activation solvent 40; a supply of an active pharmaceutical ingredient formulation 42 including an active pharmaceutical ingredient; a second inkjet applicator 28B for selectively dispensing the active pharmaceutical ingredient formulation 42; a controller 32; and a non-transitory computer readable medium having stored thereon computer executable instructions to cause the controller 32 to utilize the build material distributor 28 to dispense the build material granules 26; and utilize the first inkjet applicator 28A and the second inkjet applicator 28B to respectively and selectively dispense the activation solvent 40 and the active pharmaceutical ingredient formulation 42.

As shown in FIG. 1, the printing system 10 includes a build area platform 12, the build material supply 14 containing build material granules 16, and the build material distributor 18.

The build area platform 12 receives the build material granules 16 from the build material supply 14. The build area platform 12 may be integrated with the printing system 10 or may be a component that is separately insertable into the printing system 10. For example, the build area platform 12 may be a module that is available separately from the printing system 10. The build material platform 12 that is shown is also one example, and could be replaced with another support member, such as a platen, a fabrication/print bed, a glass plate, or another build surface.

Figure 3A:
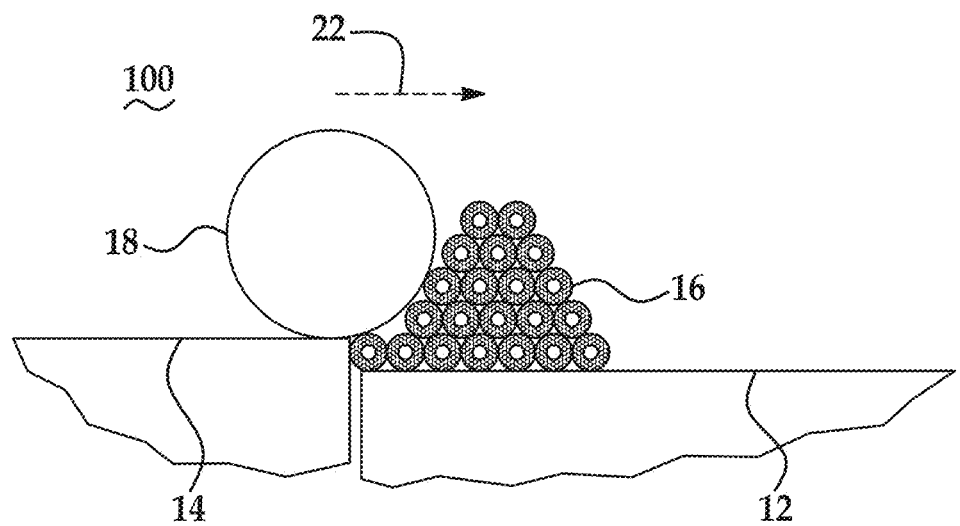
FIGS. 3A through 3K are schematic and partially cross-sectional views depicting the formation of a green part, and a pharmaceutical tablet using examples of a 3D printing method disclosed herein.
Figure 3B:
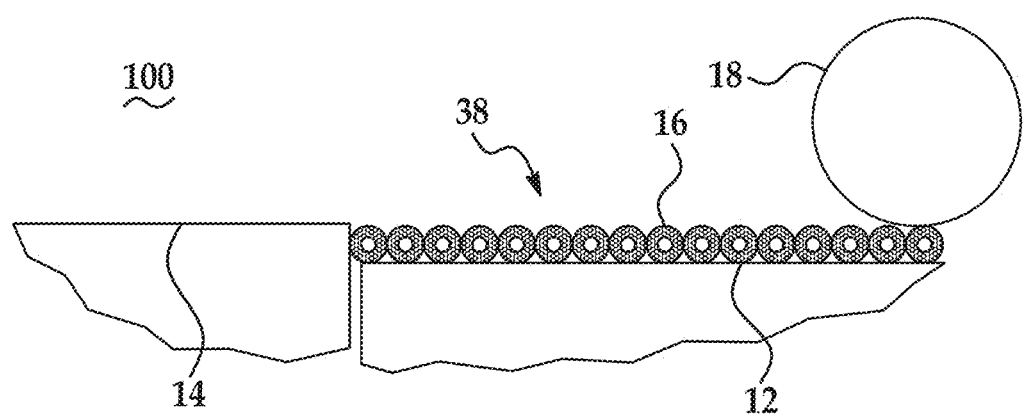
Figure 3C:
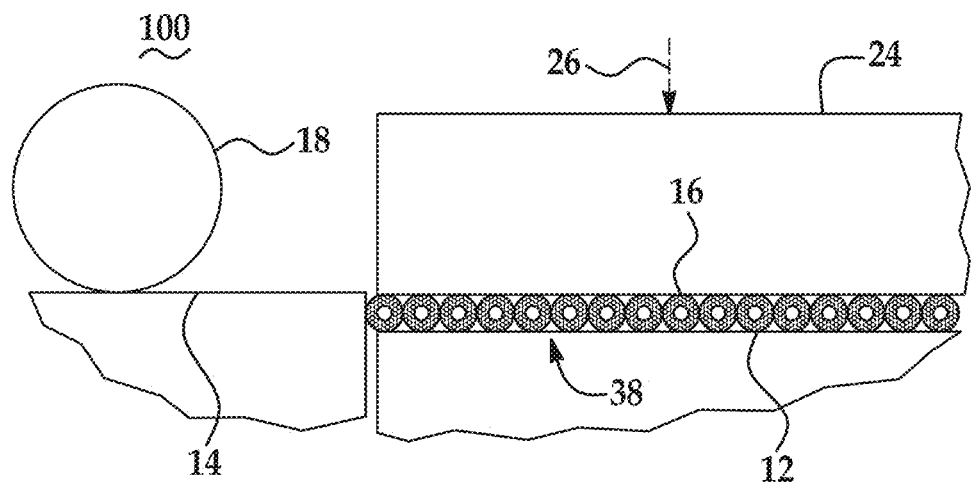
Figure 3D:
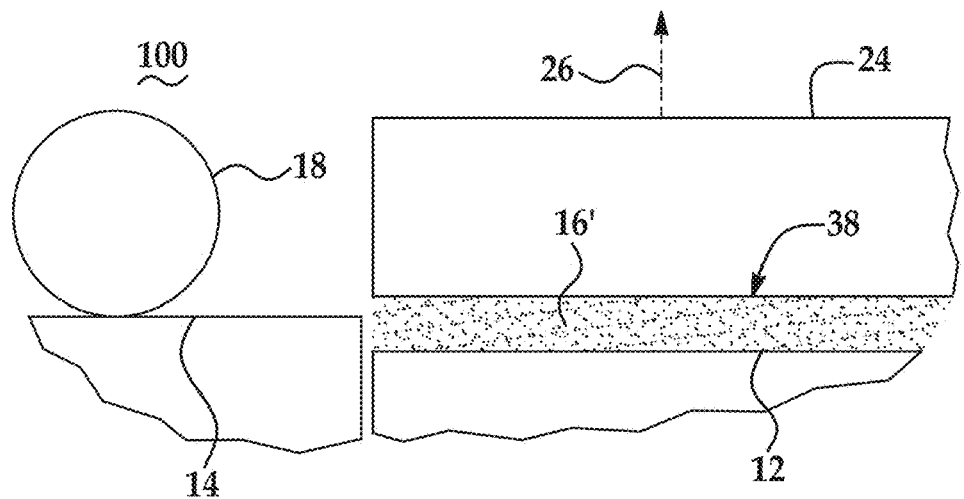
Figure 3E:
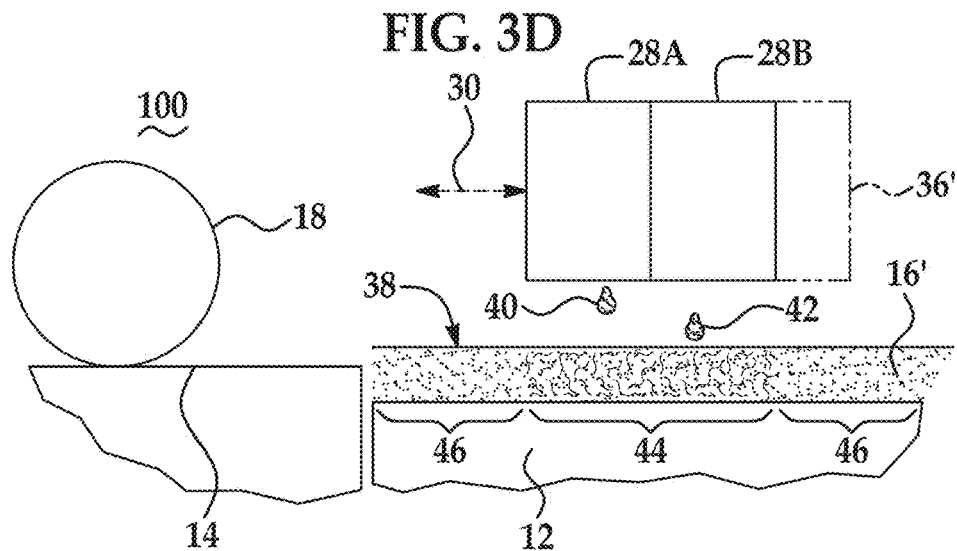
Figure 3F:
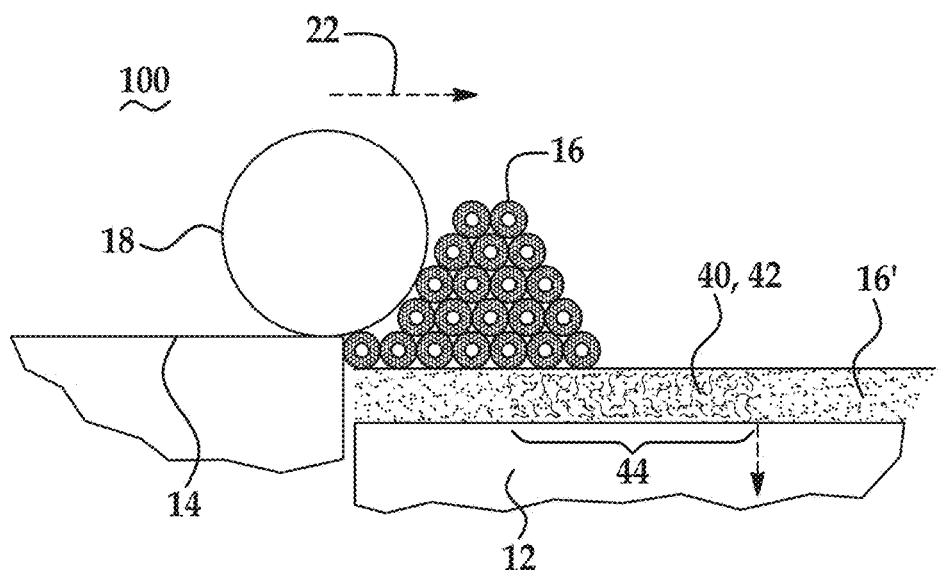

The build area platform 12 may be moved in a direction as denoted by the arrow 20, e.g., along the z-axis, so that build material granules 16 may be delivered to the platform 12 or to a previously formed layer of build material granules 16 or build material fragments 16' (see FIG. 3F). In an example, when the build material granules 16 are to be delivered, the build area platform 12 may be programmed to advance (e.g., downward) enough so that the build material distributor 18 can push the build material granules 16 onto the platform 12 to form a layer of the build material granules 16 thereon (see, e.g., FIGS. 3A and 3B). The build area platform 12 may also be returned to its original position, for example, when a new pharmaceutical tablet is to be built.

The build material supply 14 may be a container, bed, or other surface that is to store a supply of the build materials granules 16 and to position the build material granules 16 between the build material distributor 18 and the build area platform 12. In some examples, the build material supply 14 may include a surface upon which the build material granules 16 may be supplied, for instance, from a build material source (not shown) located above the build material supply 14. Examples of the build material source may include a hopper, an auger conveyer, or the like. Additionally, or alternatively, the build material supply 14 may include a mechanism (e.g., a delivery piston) to provide, e.g., move, the build material granules 16 from a storage location to a position to be spread onto the build area platform 12 or onto a previously formed layer of build material granules 16 or build material fragments 16'.

The build material distributor 18 may be moved in a direction as denoted by the arrow 22, e.g., along the y-axis, over the build material supply 14 and across the build area platform 12 to spread a layer of the build material granules 16 over the build area platform 12. The build material distributor 18 may also be returned to a position adjacent to the build material supply 14 following the spreading of the build material granules 16. The build material distributor 18 may be a blade (e.g., a doctor blade), a roller, a combination of a roller and a blade, and/or any other device capable of spreading the build material granules 16 over the build area platform 12. For instance, the build material distributor 18 may be a counter-rotating roller.

Each build material granule 16 includes a plurality of excipient particles, and at least one of the plurality of excipient particles is a latent binder. In some examples, all of the excipient particles in the granule 16 are made up of the latent binder material. In some other examples, the granule 16 may be made up of different excipient particles. In these other examples, some of the excipient particles are the latent binder, and some other of the excipient particles include an insoluble bulk filler, an additional component (e.g., antiadherent, a disintegrant, a colorant, a flavoring agent, a preservative, or combinations thereof), or combinations of these types of excipient particles.

In an example, the build material granules 16 have a granule size ranging from about 20 µm to about 400 µm. In another example, the granule size ranges from about 10 µm to about 150 µm. The term "granule size" is used herein to describe the granule build material 16. The granule size generally refers to the diameter or average diameter of the composite granule build material 16, which may vary, depending upon the morphology of the composite. In an example, a respective build material granule 16 may have a morphology that is substantially spherical. A substantially spherical granule 16 (i.e., spherical or near-spherical) has a sphericity of >0.84. Thus, any individual granules 16 having a sphericity of <0.84 are considered non-spherical (irregularly shaped). The granule size of the substantially spherical granule 16 may be provided by its largest diameter, and the granule size of a non-spherical granule 16 may be provided by its average diameter (i.e., the average of multiple dimensions across the granule 16) or by an effective diameter, which is the diameter of a sphere with the same mass and density as the non-spherical granule 16.

In some examples, the build material granule 16 has a hollow center (e.g., as shown in FIG. 3A). In other examples, the build material 12 has a substantially filled in center.

Figure 3G:
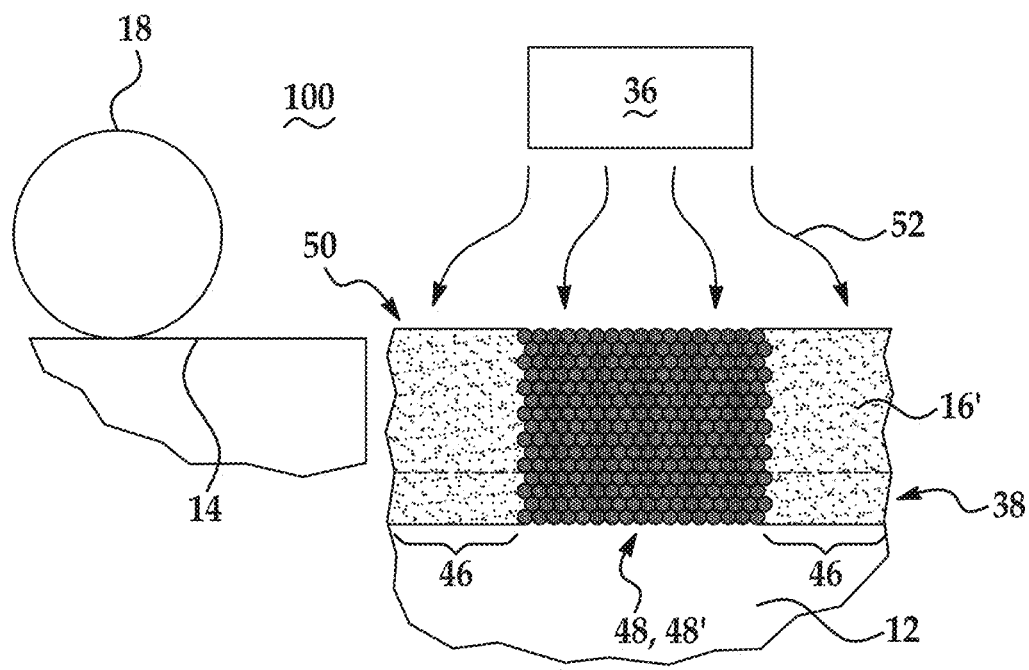

As used herein "excipient particles" may refer to the non-active ingredients among which the active pharmaceutical ingredient is placed to form the pharmaceutical tablet 48' (see FIG. 3G). Each excipient particle is edible (i.e., safe for ingestion and/or approved by the Food and Drug Administration (FDA) for ingestion), and may have high solubility or low solubility in the activation solvent 40 (see, FIG. 3E).

A wide variety of excipient particles may be used. In each example of the granule 16, at least one of the excipient particles is the latent binder.

The latent binder may be any material that i) has enough adhesive strength to hold the plurality of excipient particles together to form the granules 16 and enough mechanical stability to survive limited handling (e.g., spreading the build material granules 16 into layers), ii) is at least partially soluble in the activation solvent 40, and iii) is edible (i.e., safe for ingestion and/or approved by the FDA for ingestion). The latent binder plays a dual role in the pharmaceutical tablet 48' in that it is a structural material (i.e., filler) and also a binder (after activation).

One property of the latent binder used to form the granules 16 is that it is at least partial solubility in the activation solvent 40. The latent binder solubility in the activation solvent 40 should be higher than 0.5 wt %, when measured at a temperature corresponding to that of the printing environment (which may vary, but in some examples ranges from about 40° C. to about 50° C.). In some examples, the latent binder solubility is higher than 2 wt %. In other examples, the latent binder solubility in the activation solvent 40 is higher than 90 wt %. In still other examples, the latent binder is completely miscible in the activation solvent 40. It is to be understood that there is no upper limit on the latent binder solubility in the activation solvent 40, and the higher the solubility, the better.

The latent binder may be povidone (also known as polyvinylpyrrolidone (PVP)), polyethylene glycols of different molecular mass (PEG), co-polymers of ethylene glycol and propylene glycol, activation solvent soluble cellulose and other polysugar derivatives (e.g., hydroxypropyl cellulose (HPC), carboxymethylcellulose salts (Na-CMC), carrageenan (the hydrocolloid obtained by extraction with water or aqueous alkali from some members of the class Rhodophyceae (red seaweed), etc.), guar gum, carob bean gum, inulin, maltodextrines, complexes of cellulose derivatives, such as gum arabic, xantham gum, agar, etc., water-soluble glucuronan polymers, such as alginic acid and its salts, dextrates, dextrines, activation solvent soluble starches, activation solvent soluble starch derivatives, soluble cyclic oligosugars such as cyclodextrins, activation solvent soluble proteins (e.g., gelatin, albumin, etc.), sugars and sugar derivatives (such as sucrose, lactose, etc.), sugar alcohols (such as xylitol, sorbitol, mannitol, etc.), and combinations thereof. The latent binder may also be other conventionally approved pharmaceutical excipients that are at least partially soluble in the activation solvent 40. For example, the latent binder may be any food grade water-soluble polymer.

The latent binder may be present in the granules 16 in any amount. In an example, the amount of the latent binder present in the granules 16 ranges from about 0.1 wt % to about 100 wt % based on the total wt % of the granules 16.

In some examples, in addition to the latent binder, the granules 16 also include other excipient components (e.g., particles), such as insoluble bulk filler(s) and/or additional excipient component(s). Any combination of these excipient particles may make up the granules 16.

Insoluble bulk fillers do not act as binders in the pharmaceutical tablet 48', but rather are a structural material. Examples of suitable insoluble bulk fillers include polysaccharides, such as insoluble starches (i.e., starches that are not soluble in the activation solvent 40, e.g., water-insoluble starches, such as amylum, which is a food-grade starch that is insoluble in cold water (e.g., water at a temperature of about or below 18° C.), microcrystalline cellulose, esters of polylactic acid, food-grade clays and inorganic substances, such as bentonite, kaolin, calcium carbonate, calcium lactate, calcium silicate, calcium phosphates, etc.

The insoluble bulk fillers may be present in the granules 16 in an amount ranging from 0 wt % to about 90 wt % based on the total wt % of the granules 16.

The excipient particles may include antiadherent(s) to reduce adhesion between pressing platen(s) (e.g., pressing die 24) and the surface of the pressed build material granules 16 or crushed build material fragments 16' and/or the surface of the pharmaceutical tablet 48'. Suitable antiadherents often have low solubility in water (e.g., less than 1 wt % or less than 0.1 wt %) and are suitable for use in the food industry. Examples of suitable antiadherent(s) include fatty acid salts, such as magnesium stearate, calcium stearate, etc. Another example of a suitable antiadherent includes precipitated silica.

The antiadherent(s) may be present in the granules 16 in an amount ranging from about 0.1 wt % to about 5 wt % based on the total wt % of the granules 16.

The excipient particles may include disintegrant(s). Disintegrants are solid particles that significantly swell upon contact with moisture. The expansion of the disintegrant(s) may cause the pharmaceutical tablet 48' to break up in the digestive tract and thus, may speed up the release of the active pharmaceutical ingredient for absorption. The disintegrant(s) may swell upon contact with the activation solvent 40 and/or a solvent of the active pharmaceutical ingredient formulation 42. However, as the activation solvent 40 and/or other solvent(s) evaporate, the swelling of the disintegrant(s) decreases, and the pharmaceutical tablet 48' forms with the disintegrant(s) unexpanded. Examples of suitable disintegrants may be produced by cross-linking water-soluble polymers. Specific examples include cross-linked polyvinylpyrrolidone (PVP) and internally cross-linked sodium carboxymethyl cellulose (Na-Croscarmellose). Other examples of suitable disintegrants include some starch derivatives, such as sodium starch glycolate.

In some examples, a single component may act as both the latent binder and the disintegrant. In these examples, the amount of the disintegrant(s) present in the granules 16 may range from about 1 wt % to about 100 wt % based on the total wt % of the granules 16.

The excipient particles may include colorant(s) to improve the appearance of the pharmaceutical tablet 48', to conform to customer expectations (e.g., to render the pharmaceutical tablet 48' a color that is associated with a flavor of the pharmaceutical tablet 48'), and/or to communicate tablet information (e.g., to render the pharmaceutical tablet 48' the color associated with an active pharmaceutical ingredient, a dosage, etc.). As one example, titanium dioxide ($TiO_2$) may be used as the colorant to produce a white pharmaceutical tablet 48'. In other examples, food grade dyes, such as FD&C Blue No. 1 (Brilliant Blue FCF), FD&C Blue No. 2 (Indigotine), FD&C Green No. 3 (Fast Green FCF), FD&C Red No. 3 (Erythrosine), FD&C Red No. 40 (Allura Red AC), FD&C Yellow No. 5 (Tartrazine), FD&C Yellow No. 6 (Sunset Yellow FCF), or combinations thereof, may be used as the colorant(s) to produce a desired colored appearance.

The colorant(s) may be present in the granules 16 in an amount ranging from about 0.1 wt % to about 5 wt % based on the total wt % of the granules 16.

The excipient particles may include flavoring agent(s). Flavoring agent(s) may be used to introduce a desired flavor to the pharmaceutical tablet 48' and/or to mask an unpleasant flavor of an ingredient of the pharmaceutical tablet 48' (e.g., an unpleasant flavor inherent to the active pharmaceutical ingredient). Suitable flavoring agent(s) may be natural ingredients, such as fruit or plant extracts, or artificial ingredients, such as malic acid(hydroxybutanedioic acid), leucine, adipic acid, denatonium benzoate, ethyl lactate, ethyl maltol, ethyl vanillin, vanillin, fumaric acid, maltol, menthol, methionine, monosodium glutamate, propyl gallate, sodium lactate, tartaric acid, thymol, triethyl citrate, etc.

The flavoring agent(s) may be present in the granules 16 in any suitable amount for a particular flavoring agent. For example, some flavoring agent(s) may become toxic at certain levels, and thus these flavoring agent(s) may be included in an amount that is below the concentration at which the flavoring agent(s) would become toxic. In an example, the amount of the flavoring agent(s) present in the granules 16 ranges from about 1 parts per million (ppm) by weight to about 100 ppm by weight based on the total parts of the granules 16. In other instances, the flavoring agent may be present in an amount up to about 5 wt % of the total wt % of the granules 16.

The excipient particles may include preservative(s) to prolong the useful life of the pharmaceutical tablet 48'. The preservative(s) may slow the degradation of the active pharmaceutical ingredient during tablet storage. Examples of suitable preservatives include anti-oxidant species, such as vitamin A, vitamin E, vitamin C, citric acid and sodium citrate. Other examples of suitable preservatives include anti-fungal species, such as parabens.

The amount of preservative(s) that may be present in the granules 16 may depend, in part, on the preservative(s) used. For example, when a species that may be toxic at high concentrations (e.g., some anti-fungal species) is used, the preservative(s) may be present in the granules 16 in an amount that ranges from 0 wt % to about 0.01 wt % (or below the concentration at which the species becomes toxic). As another example, when vitamin A, vitamin E, and/or vitamin C is/are used, the preservative(s) may be present in the granules 16 in an amount that ranges from 0.01 wt % to about 5 wt %.

In an example of the granule 16, the latent binder is selected from the group consisting of povidone, polyethylene glycol (PEG), activation solvent soluble cellulose derivatives, activation solvent soluble starches, activation solvent soluble starch derivatives, activation solvent soluble proteins, sugars, sugar derivatives, sugar alcohols, and combinations thereof; and at least one other of the plurality of excipient particles includes: an insoluble bulk filler selected from the group consisting of microcrystalline cellulose, activation solvent insoluble polysaccharides, and combinations thereof; an additional component selected from the group consisting of an antiadherent, a disintegrant, a colorant, a flavoring agent, a preservative, and combinations thereof; or combinations thereof (i.e., any combinations of the listed insoluble bulk fillers and/or the listed additional components).

In another example, each of the plurality of excipient particles (making up the granule 16) is the latent binder, and the latent binder is selected from the group consisting of povidone, polyethylene glycol (PEG), activation solvent soluble cellulose derivatives, activation solvent soluble starches, activation solvent soluble starch derivatives, activation solvent soluble proteins, sugars, sugar derivatives, sugar alcohols, and combinations thereof.

The excipient particles may have a particle size that ranges from about 0.5× (i.e., 0.5 times) to about 0.1× the granule diameter. In an example, the particle size of the excipient particles ranges from 0.1 μm to about 200 μm. In another example, the particle size ranges from 0.5 μm to about 40 μm. The particle size of the excipient particles generally refers to the diameter or average diameter of the excipient particle, which may vary, depending upon the morphology of the particle. In an example, a respective excipient particle may have a morphology that can form flowable and/or spreadable granules 16. The particle size of a substantially spherical excipient particle may be provided by its largest diameter, and the particle size of a non-spherical excipient particle may be provided by its average diameter (i.e., the average of multiple dimensions across the particle) or by an effective diameter, which is the diameter of a sphere with the same mass and density as the non-spherical particle.

The excipient particles (at least one of which includes the latent binder) may be similarly sized particles or differently sized particles.

When each of the excipient particles in a granule 16 is the latent binder, 100 wt % of the granule 16 is latent binder. When the granule 16 is made up of latent binder and another type of excipient (e.g., insoluble bulk filler, other additives, or combinations thereof), the granule 16 may include the latent binder in an amount ranging from about 0.1 wt % to about 99 wt % based on the wt % of the other excipient particle(s) in each granule 16.

Some example formulations of the build material granules 16 are shown in Table 1 below.

TABLE 1

| Ingredient | Specific component | Formulation 1 (wt %) | Formulation 2 (wt %) | Formulation 3 (wt %) | Formulation 4 (wt %) |
|---|---|---|---|---|---|
| Latent Binder | Povidone | 5 | 25 | 5 | 5 |
| Insoluble Bulk Filler | Microcrystalline cellulose | 93 | 73 | 89 | 84 |

TABLE 1-continued

| Ingredient | Specific component | Formulation 1 (wt %) | Formulation 2 (wt %) | Formulation 3 (wt %) | Formulation 4 (wt %) |
|---|---|---|---|---|---|
| Antiadherent | Magnesium stearate | 2 | — | 1 | 1 |
|  | Precipitated silica | — | 2 | 2 | 2 |
| Disintegrant | Na-Croscarmellose | — | — | 3 | 3 |
| Colorant | FD&C Yellow No. 5 | — | — | — | 5 |

The granules 16 may be produced via any suitable method, such as spray drying, freeze spraying with subsequent freeze-drying, or any other suitable wet granulation technology.

The printing system 10 also includes a pressing die 24. The pressing die 24 may be positioned a spaced distance from the build area platform 12 along the z-axis, but close enough so that it can be moved into contact with the platform 12. The pressing die 24 may be lowered as denoted by the arrow 26, e.g., along the z-axis, to contact and apply pressure onto a layer of the build material granules 16 that has been formed on the surface of the build area platform 12.

In an example, the pressing die 24 may apply sufficient pressure onto the layer of the build material granules 16 to crush the build material granules 16 into build material fragments 16' (which may include intact excipient particles, such as latent binder alone or in combination with other excipients), and to increase the density of the layer. In another example, the pressing die 24 may apply sufficient pressure onto the layer of the build material granules 16 to tighten the packing of the build material granules 16 (without crushing them), and to increase the density of the layer. As mentioned above, pressure may be applied to tighten the packing of the build material granules 16 when a more porous and less dense pharmaceutical tablet is desired, and pressure may be applied to crush the build material granules 16 when a less porous and denser pharmaceutical tablet is desired.

The amount of pressure that is applied may depend, at least in part, on the excipient particles used in the granules 16 and/or whether the pressure is being applied to tighten the packing of the build material granules 16 or to crush them. In an example, the pressure that is applied to the granules 16 by the pressure die 24 ranges from about 20 psi to about 10,000 psi. In another example, the pressure applied to the build material granules 16 ranges from about 20 psi to about 1,000 psi. When the pressure is applied to tighten the packing of the build material granules 16 but not crush them, the pressure that is applied to the granules 16 may range from about 20 psi to about 200 psi. In an example the amount of pressure may be about 30 psi. When the pressure is applied to crush the build material granules 16, the pressure that is applied to the granules 16 may be as low as about 100 psi, or may range from about 200 psi or higher, e.g., to about 1,000 psi or to about 10,000 psi. The amount of pressure required to crush the granules 16 may depend, in part, on one or more of: the process used to prepare the granules 16, the amount of latent binder in the granules 16, and whether the pressure is applied before or after the activation solvent 40 is selectively applied.

As shown in FIG. 1, the printing system 10 also includes a first inkjet applicator 28A, which may contain the activation solvent 40 (shown in FIG. 3E), and second applicator 28B, which may contain the active pharmaceutical ingredient formulation 42 (shown in FIG. 3E).

The activation solvent 40 is capable of at least partially dissolving the latent binder in the pressed and/or crushed build material granules 16, 16'. The activation solvent 40 is also relatively volatile such that it can be evaporated during the printing process. The activation solvent 40 and each of its components are edible (i.e., safe for ingestion and/or approved by the FDA for ingestion).

The activation solvent 40 may include water and/or ethanol. In another example, the activation solvent 40 consists of ethanol with no other components. In still another example, the activation solvent 40 consists of water with no other components. It is to be understood that other activation solvents 40 may be used, such as ethyl acetate, acetone, or other volatile solvents, as long as these solvents can be removed during formation of the tablet 48'.

In some examples, the activation solvent 40 may also include a food grade surface active species, such as a monoglyceride, a diglyceride, lecithin, or a combination thereof. In these examples, the surface active species may be added to the activation solvent 40 to facilitate wetting of the excipient particles in the granules 16/fragments 16'.

In an example, the activation solvent 40 consists of water, or the activation solvent includes a monoglyceride, a diglyceride, lecithin, or a combination thereof.

In other examples, the activation solvent 40 may exclude a binder. By excluding a binder, the activation solvent 40 may be easily jetted from the first inkjet applicator 28A.

The active pharmaceutical ingredient formulation 42 includes at least the active pharmaceutical ingredient, which is biologically active. Any active pharmaceutical ingredient that can be dissolved or dispersed in a liquid vehicle and that can be jetted can be used.

The active pharmaceutical ingredient may be present in the active pharmaceutical ingredient formulation 42 in an amount ranging from about 1 wt % to about 80 wt % based on the total wt % of the active pharmaceutical ingredient formulation 42. In an example, active pharmaceutical ingredient is present in an amount ranging from about 70 wt % to about 80 wt % based on the total wt % of the active pharmaceutical ingredient formulation 42.

The active pharmaceutical ingredient formulation 42 may also include a liquid vehicle. In some examples, the active pharmaceutical ingredient formulation 42 consists of the active pharmaceutical ingredient and the liquid vehicle with no other components.

As used herein, "liquid vehicle" may refer to the liquid fluid in which the active pharmaceutical ingredient is placed to form the active pharmaceutical ingredient formulation 42. Each component of the liquid vehicle is edible (i.e., safe for ingestion and/or approved by the FDA for ingestion). A wide variety of liquid vehicles may be used to form the active pharmaceutical ingredient formulation 42. The liquid vehicle may include a solvent in which the active pharmaceutical ingredient may be dissolved or dispersed. In some examples, the liquid vehicle consists of the solvent with no other components.

The solvent of the liquid vehicle is food compatible and relatively volatile such that it can be evaporated during the printing process. The solvent used will depend, at least in part, on the active pharmaceutical ingredient that is used. Examples of the solvent include water, ethanol, and combinations thereof. Other examples of the solvent include some FDA-approved, food grade, high boiling solvent(s), such as glycerin, which can be used as a humectant for improving jetting reliability of the active pharmaceutical ingredient formulation 42. In some examples, the FDA-approved, food grade, high boiling solvent may be present in the active pharmaceutical ingredient formulation 42 in an amount ranging from 0 wt % to about 30 wt % based on the total wt % of the active pharmaceutical ingredient formulation 42. In these examples, another solvent, such as water or ethanol, may also be included in the active pharmaceutical ingredient formulation 42, or the active pharmaceutical ingredient may make up the balance of the active pharmaceutical ingredient formulation 42.

In some examples, the active pharmaceutical ingredient formulation 42 excludes a binder. By excluding a binder, the pharmaceutical ingredient formulation 42 may be easily jetted from the second inkjet applicator 28B. In some examples, the activation solvent 40 and the active pharmaceutical ingredient formulation 42 each exclude a binder.

In some examples, the system 10 and method disclosed herein may include another or second active pharmaceutical ingredient formulation (not shown). The other or second active pharmaceutical ingredient formulation includes at least another or second active pharmaceutical ingredient, which is biologically active. The other or second active pharmaceutical ingredient included in the other or second active pharmaceutical ingredient formulation may be different than the active pharmaceutical ingredient included in the active pharmaceutical ingredient formulation 42. Utilizing different active pharmaceutical ingredients may allow one to create pharmaceutical tablets 48' with different active pharmaceutical ingredients in the same or different regions (e.g., in the x-y plane) or in different layers (e.g., in the z-direction).

The other or second active pharmaceutical ingredient formulation may also include a liquid vehicle. The liquid vehicle used in the other or second active pharmaceutical ingredient formulation may be any of the liquid vehicles described in reference to the active pharmaceutical ingredient formulation 42. In some examples, the other or second active pharmaceutical ingredient formulation consists of the other or second active pharmaceutical ingredient and the liquid vehicle with no other components. In other examples, the other or second active pharmaceutical ingredient formulation excludes a binder. By excluding a binder, the other or second pharmaceutical ingredient formulation may be easily jetted from an inkjet applicator. While one additional active pharmaceutical ingredient formulation has been described, it is to be understood that examples of the system 10 and method disclosed herein may include and/or utilize any desirable number of different active pharmaceutical ingredient formulations.

In the examples in which the system 10 and method include the other or second active pharmaceutical ingredient formulation, another (e.g., third) inkjet applicator (not shown) may apply the other or second active pharmaceutical ingredient formulation. The third inkjet applicator may be a separate cartridge (for dispensing the other or second active pharmaceutical ingredient formulation) within the first inkjet applicator 28A or the second inkjet applicator 28B, or it may be a separate inkjet applicator.

In some examples, the system 10 and method disclosed herein may include a food grade colorant solution. The food grade colorant solution may be used to create custom labels on the 3D printed pharmaceutical tablets 48'.

The food grade colorant solution may a colorant. The colorant included in the food grade colorant solution may be any of the colorants (e.g., food dye, pigments) described herein that may be included in the excipient particles.

The food grade colorant solution may also include a solvent that dissolves or disperses the colorant. The solvent used in the food grade colorant solution may be any of the solvents described in reference to the liquid vehicle of the active pharmaceutical ingredient formulation 42. In some examples, the food grade colorant solution consists of the colorant and the solvent with no other components. In other examples, the food grade colorant solution excludes a binder. By excluding a binder, the food grade colorant solution may be easily jetted from an inkjet applicator.

In the examples in which the system 10 and method include the food grade colorant solution, another (e.g., fourth) inkjet applicator (not shown) may apply the food grade colorant solution. The fourth inkjet applicator may be a separate cartridge (for dispensing the food grade colorant solution) within the first inkjet applicator 28A or the second inkjet applicator 28B, or it may be a separate inkjet applicator.

The activation solvent 40 and the liquid vehicle of the active pharmaceutical ingredient formulation 42 may be the same or different. When the solvent and the liquid vehicle are the same, the activation solvent 40 and the active pharmaceutical ingredient (API) formulation 42 may be combined into a single activation/API formulation, in which the activation solvent dissolves or disperses the active pharmaceutical ingredient. In these examples, the amount of the single activation/API formulation that is dispensed will control the latent binder activation as well as the amount of the active pharmaceutical ingredient that is applied.

In the examples in which activation solvent 40 and the active pharmaceutical ingredient formulation 42 are a single formulation, one inkjet applicator 28A or 28B may be used.

If it is desirable to decouple the extent of latent binder activation from the amount of the active pharmaceutical ingredient that is applied, a different activation solvent 40 and active pharmaceutical ingredient formulation 42 may be used (even if the solvents in the two formulations 40, 42 are the same). Additionally, it may be desirable for the activation solvent 40 to be separate and distinct from the active pharmaceutical ingredient formulation 42 when a region (e.g., a shell region) of the pharmaceutical tablet is not to contain the active pharmaceutical ingredient. When the activation solvent 40 is a separate and distinct formulation from the active pharmaceutical ingredient formulation 42, the solvent in the respective formulations may be the same or different. As an example, the activation solvent 40 may be separate and distinct from the active pharmaceutical ingredient formulation 42 when the latent binder has poor solubility in the solvent(s) in which the active pharmaceutical ingredient is soluble or dispersible.

The inkjet applicator(s) 28A, 28B may be scanned across the build area platform 12 in the direction indicated by the arrow 30, e.g., along the y-axis. The inkjet applicator(s) 28A, 28B may be, for instance, a thermal inkjet printhead, a piezoelectric printhead, etc., and may extend a width of the build area platform 12. While a single inkjet applicator is shown in FIG. 1 for each of the applicators 28A, 28B, it is to be understood that multiple inkjet applicators 28A, 28B may be used that span the width of the build area platform 12. Additionally, the inkjet applicators 28A, 28B may be positioned in multiple printbars. The inkjet applicator(s) 28A, 28B may also be scanned along the x-axis, for instance, in configurations in which the inkjet applicator(s) 28A, 28B does/do not span the width of the build area platform 12 to enable the inkjet applicator(s) 28A, 28B to deposit the activation solvent 40 and the active pharmaceutical ingredient formulation 42 (respectively) over a large area of a layer of build material granules 16/fragments 16'. The inkjet applicator(s) 28A, 28B may thus be attached to a moving XY stage or a translational carriage (neither of which is shown) that moves the inkjet applicator(s) 28A, 28B adjacent to the build area platform 12 in order to deposit the activation solvent 40 and the active pharmaceutical ingredient formulation 42 (respectively) in predetermined areas of a layer of the build material granules 16/fragments 16' that has been formed on the build area platform 12 in accordance with the method(s) disclosed herein. The inkjet applicator(s) 28A, 28B may include a plurality of nozzles (not shown) through which the activation solvent 40 and the active pharmaceutical ingredient formulation 42 (respectively) are to be ejected.

Each of these physical elements may be operatively connected to a controller 32 of the printing system 10. The controller 32 may control the operations of the build area platform 12, the build material supply 14, the build material distributor 18, the pressing die 24, and the inkjet applicators 28A, 28B. As an example, the controller 32 may control actuators (not shown) to control various operations of the 3D printing system 10 components. The controller 32 may be a computing device, a semiconductor-based microprocessor, a central processing unit (CPU), an application specific integrated circuit (ASIC), and/or another hardware device. Although not shown, the controller 32 may be connected to the 3D printing system 10 components via communication lines.

The controller 32 manipulates and transforms data, which may be represented as physical (electronic) quantities within the printer's registers and memories, in order to control the physical elements to create the pharmaceutical tablet 48'. As such, the controller 32 is depicted as being in communication with a data store 34. The data store 34 may include data pertaining to a pharmaceutical tablet 48' to be printed by the 3D printing system 10. The data for the selective delivery of the build material granules 16, the activation solvent 40, the active pharmaceutical ingredient formulation 42, etc. may be derived from a model of the pharmaceutical tablet 48' to be formed. For instance, the data may include the locations on each layer of build material granules 16/fragments 16' that the first inkjet applicator 28A is to deposit the activation solvent 40 and locations that the second inkjet applicator 28B is to deposit the active pharmaceutical ingredient formulation 42. In one example, the controller 32 may use the data to control the first inkjet applicator 28A to selectively apply the activation solvent 40. In another example, the controller 32 may use the data to control the second inkjet applicator 28B to selectively apply the active pharmaceutical ingredient formulation 42. The data store 34 may also include machine/computer readable instructions (stored on a non-transitory computer readable medium) that are to cause the controller 32 to utilize the build material distributor to dispense the build material granules 16, and the utilize the first inkjet applicator 28A and the second inkjet applicator 28B to respectively and selectively dispense the activation solvent 40 and the active pharmaceutical ingredient formulation 42. The data store 34 may also include machine/computer readable instructions (stored on a non-transitory computer readable medium) that are to cause the controller 32 to control the amount of build material granules 16 that is supplied by the build material supply 14, the movement of the build area platform 12, the movement of the build material distributor 18, the movement of the pressing die 24, the movement of the inkjet applicators 28A, 28B, etc.

As shown in FIG. 1, the printing system 10 may also include a heater 36, 36'. In some examples, the heater 36 includes a conventional furnace or oven, a microwave, or devices capable of hybrid heating (i.e., conventional heating and microwave heating). This type of heater 36 may be used for heating each layer 38 after the activation solvent 40 and the active pharmaceutical ingredient formulation 42 have been applied thereto, or for heating the entire pressed cake 46 (see FIG. 3G) after the printing is finished. While not shown, the heater 36 may be integrated into the build material platform 12 to provide radiative heating, conductive heating, or the like. In an example, the heater 36 may be placed below the build area platform 12. In other examples, the heater 36' may be a radiative heat source (e.g., a curing lamp) that is positioned to heat each layer 38 (see FIG. 3E) after the activation solvent 40 and the active pharmaceutical ingredient formulation 42 have been applied thereto. In the example shown in FIG. 1, the heater 36' is attached to the side of the inkjet applicators 28A, 28B, which allows for printing and heating in a single pass.

Referring now to FIG. 2 and FIGS. 3A through 3K, an example of the 3D printing method 100 is depicted. Prior to execution of the method 100 or as part of the method 100, the controller 32 may access data stored in the data store 34 pertaining to a pharmaceutical tablet 48' that is to be printed. The controller 32 may determine the number of layers of build material granules 16 that are to be formed and compressed, the locations at which the activation solvent 40 from the inkjet applicator 28A is to be deposited on each of the respective layers, and the locations at which the active pharmaceutical ingredient formulation 42 from the inkjet applicator 28B is to be deposited on each of the respective layers.

Briefly, the method 100 includes: applying build material granules 16, each of the build material granules 16 including a plurality of excipient particles, wherein at least one of the plurality of excipient particles is a latent binder (reference numeral 102); applying pressure to the build material granules 16 (reference numeral 104); selectively applying an activation solvent 40 on at least a portion of the pressed build material granules 16 (reference numeral 106); selectively applying an active pharmaceutical ingredient formulation 42 including an active pharmaceutical ingredient on the at least the portion of the pressed build material granules 16 (reference numeral 108); and evaporating the activation solvent 40 (reference numeral 110).

Figure 2:
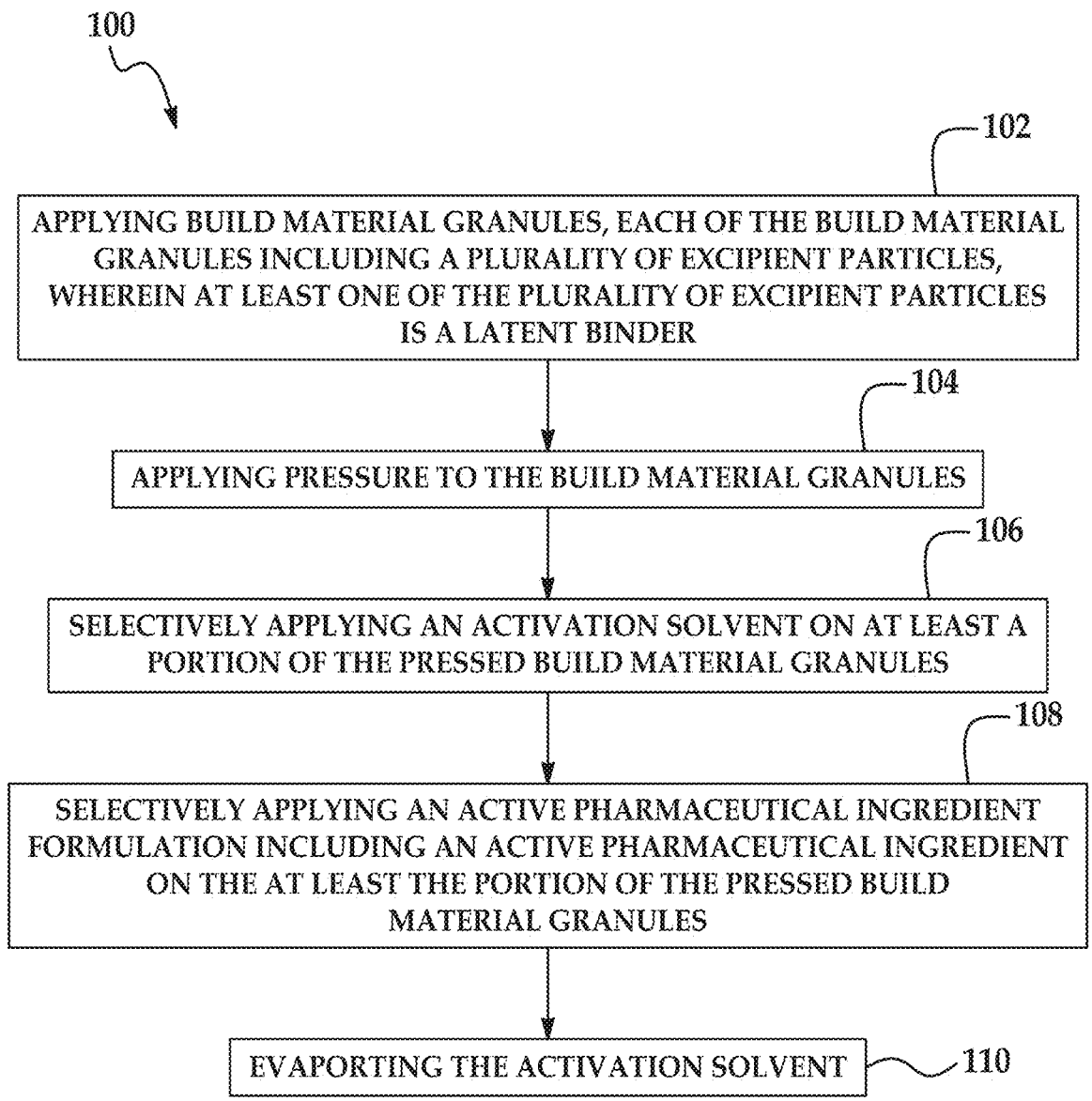
FIG. 2 is a flow diagram illustrating an example of a 3D printing method disclosed herein.

As shown at reference numeral 102 in FIG. 2 and in FIGS. 3A and 3B, the method 100 includes applying the build material granules 16 (wherein each of the build material granules 16 includes a plurality of excipient particles, and at least one of the plurality of excipient particles is a latent binder). In FIG. 3A, the build material supply 14 may supply the build material granules 16 into a position so that they are ready to be spread onto the build area platform 12. In FIG. 3B, the build material distributor 18 may spread the supplied build material granules 16 onto the build area platform 12. The controller 32 may execute control build material supply instructions to control the build material supply 14 to appropriately position the build material granules 16, and may execute control spreader instructions to control the build material distributor 18 to spread the supplied build material granules 16 over the build area platform 12 to form a layer 38 of build material granules 16 thereon. As shown in FIG. 3B, one layer 38 of the build material granules 16 has been applied.

The layer 38 has a substantially uniform thickness across the build area platform 12. In an example, the thickness of the layer 38 ranges from about 50 µm to about 300 µm, although thinner or thicker layers may also be used. For example, the thickness of the layer 36 may range from about 20 µm to about 800 µm, or from about 40 µm to about 300 µm. The layer thickness may be about 2× the granule diameter at a minimum for finer tablet definition. In some examples, the layer thickness may be about 1.2× the granule diameter.

While not shown in FIG. 2 or 3A through 3K, the method 100 may include preparing the build material granules 16 prior to applying the build material granules 16. In an example, preparing the build material granules 16 may include dissolving the latent binder, alone or in combination with another soluble excipient component, in an aqueous liquid. The aqueous liquid may be water. In this example, the aqueous liquid (containing the latent binder) may then be converted into dry granular powder by spray drying or freeze spraying with subsequent freeze-drying the aqueous liquid containing the latent binder. In another example, preparing the build material granules 16 may include dissolving the latent binder, alone or in combination with another soluble excipient component, in an aqueous liquid; dispersing an insoluble excipient component in the aqueous liquid; and spray drying or freeze spraying with subsequent freeze-drying the aqueous liquid containing the latent binder, the soluble excipient component, and the insoluble excipient component, thereby creating the build material granules 16. As noted, when other, insoluble excipient(s) is/are utilized, the preparation of the build material granules 16 may further include dispersing the insoluble excipient component in the aqueous liquid (which already contains the latent binder, alone or in combination with another soluble excipient component). In these examples, a slurry may be produced. The slurry (containing the latent binder, and at least one insoluble excipient component) may then be converted into dry granular powder by spray drying or freeze spraying with subsequent freeze-drying the slurry containing the latent binder, the soluble excipient component, and the insoluble excipient component. The spray drying or freeze spraying with subsequent freeze-drying forms/creates the build material granules 16. Other suitable wet granulation technology may also be used to covert the slurry or the aqueous liquid containing the latent binder and, in some instances, other soluble and/or insoluble excipient component(s) into dry granular powder.

As shown at reference numeral 104 in FIG. 2 and in FIGS. 3C and 3D, the method 100 continues by applying pressure to the build material granules 16 (FIG. 3C). The pressure may be applied in order to tighten the packing of the build material granules 16 (without crushing them), or the pressure may be applied in order to crush, break up, pulverize, etc. the granules 16 to form build material fragments 16' (FIG. 3D). As such, in some examples, the applying of the pressure to the build material granules 16 forms crushed build material granules (i.e., fragments 16'). The fragments 16' may include individual excipient particles and/or some excipient particles that are still bound together.

In the example shown in FIG. 3C, the pressing die 24 is moved in the direction indicated by the arrow 26 until it contacts and applies a sufficient force onto the layer 36 of build material granules 16. The pressure die 24 may be responsive to the controller 32 which executes pressing die instructions. FIG. 3D illustrates the removal of the pressing die 24 after the build material granules 16 have been pressed or crushed.

The application of pressure may be accomplished in other manners. For instance, instead of moving the pressing die 24 in the direction denoted by the arrow 26, the build area platform 12 may be moved in a direction opposite direction to that denoted by the arrow 26 in FIG. 3C. In other words, the build area platform 12 may be moved toward the pressing die 24 such that pressure is applied onto the build material granules 16 by the movement of the build area platform 12. In another example, the build material distributor 18 may apply the pressure to the granules 16. For instances, the build material distributor 18 may apply the sufficient amount of pressure during an initial pass over the layer 38, or during a second or subsequent pass over the build area platform 12 after having spread the granules 16, e.g., during a return trip back to its original position.

Through application of the pressure by the pressing die 24 and an opposing pressure applied by the build area platform 12, the density of the layer 38 may also be increased. When the granules 16 are pressed and/or crushed, voids within and/or between the granules 16 are reduced or eliminated. This densifies the layer 38, which may improve a density of the final pharmaceutical tablet 48'. The pressed layer 38 may also be in a form that is more receptive to receive the activation solvent 40 and the active pharmaceutical ingredient formulation 42.

It is to be understood that, while the build material fragments 16' are shown in FIGS. 3D through 3K, in some examples of the method 100, the build material granules 16 are not crushed during the pressure application. In these examples, the build material granules 16 remain intact and would be present in the layer 38, rather than the build material fragments 16' shown in FIG. 3D. It is to be further understood that throughout FIGS. 3E through 3K and reference numerals 106 through 110 of FIG. 2, where reference is made to the build material fragments 16', the pressed build material granules 16 may be used instead.

As shown at reference numerals 106 and 108 in FIG. 2, the method 100 continues by selectively applying the activation solvent 40 on at least a portion of the pressed build material granules, and selectively applying the active pharmaceutical ingredient formulation 42 (including the active pharmaceutical ingredient) on the at least the portion of the pressed build material granules. It is to be understood that the pressed build material granules may refer to the pressed (but otherwise intact) granules 16 or the build material fragments 16'.

The selective application of each of the activation solvent 40 and the active pharmaceutical ingredient formulation 42 on a portion 44 of the build material fragments 16' is shown in FIG. 3E. As illustrated in FIG. 3E, the activation solvent 40 may be dispensed from the inkjet applicator 28A, and the active pharmaceutical ingredient formulation 42 may be dispensed from the inkjet applicator 28B. In an example, the activation solvent 40 may be dispensed onto the portion 44 first, and then the pharmaceutical ingredient formulation 42 may be dispensed onto the portion 44. In another example, the activation solvent 40 and the pharmaceutical ingredient formulation 42 may be dispensed at least substantially simultaneously (e.g., one immediately after the other in a single printing pass, or at the same time).

Although shown as separate applicators 28A, 28B, it is to be understood that a single applicator with individual cartridges for dispensing the respective fluids 40, 42 may be used. In still other examples, a single applicator 28A or 28B with a single cartridge may be used to dispense a single activation/API formulation. When the single activation/API formulation (which combines the activation solvent 40 and the active pharmaceutical ingredient formulation 42) is used, the selective application is accomplished in a single step.

The applicators 28A and/or 28B may each be a thermal inkjet printhead, a piezoelectric printhead, etc., and the selectively applying of the activation solvent 40 and the selectively applying of the active pharmaceutical ingredient formulation 42 may each be accomplished by the associated inkjet printing technique.

The controller 32 may execute instructions to control the inkjet applicator 28A (e.g., in the directions indicated by the arrow 30) to deposit the activation solvent 40 onto predetermined portion(s) 44 of the fragments 16' that are to become part of the pharmaceutical tablet 48'. The inkjet applicator 28A may be programmed to receive commands from the controller 32 and to deposit the activation solvent 40 according to a pattern of a cross-section for the layer of the pharmaceutical tablet 48' that is to be formed. As used herein, the cross-section of the layer of the pharmaceutical tablet 48' to be formed refers to the cross-section that is parallel to the surface of the build area platform 12. In the example shown in FIG. 3E, the inkjet applicator 28A selectively applies the activation solvent 40 on those portion(s) 44 of the layer 38 that is/are to become the first layer of the pharmaceutical tablet 48'. As an example, if the pharmaceutical tablet 48' that is to be formed is to be shaped like a cylinder, the activation solvent 40 will be deposited in a circular pattern (from a top view) on at least a portion of the layer 38 of the build material fragments 16'. The activation solvent 40 may also be dispensed to form an oval tablet 48'. In the example shown in FIG. 3E, the activation solvent 40 is deposited on the portion 44 of the layer 38 and not on the portions 46.

The controller 32 may also execute instructions to control the inkjet applicator 28B (e.g., in the directions indicated by the arrow 30) to deposit the active pharmaceutical ingredient formulation 42 onto predetermined portion(s) 44 of the fragments 16' that are to contain the active pharmaceutical ingredient. The inkjet applicator 28B may be programmed to receive commands from the controller 32 and to deposit the active pharmaceutical ingredient formulation 42 according to a pattern of a cross-section for the region (of the layer of the pharmaceutical tablet 48' that is to be formed) that is to contain the active pharmaceutical ingredient. In the example shown in FIG. 3E, the inkjet applicator 28B selectively applies the active pharmaceutical ingredient formulation 42 on those portion(s) 44 of the layer 38 that are to contain the active pharmaceutical ingredient in the first layer of the pharmaceutical tablet 48'. In the example shown in FIG. 3E, the active pharmaceutical ingredient formulation 42 is deposited in a circular pattern on the portion 44 of the layer 38 and not on the portions 46.

As mentioned above, the activation solvent 40 i) is capable of at least partially dissolving the latent binder in the pressed and/or crushed build material granules 16, 16', ii) is also relatively volatile such that it can be evaporated during the printing process, and iii) is edible (i.e., safe for ingestion and/or approved by the FDA for ingestion).

Since the latent binder is at least partially soluble in the activation solvent 40, the selective application of the activation solvent dissolves the latent binder. When the activation solvent 40 is selectively applied in the desired portion(s) 44, the activation solvent 40 penetrates into the layer 38 and the latent binder of the fragments 16' in contact with the activation solvent 40 at least partially dissolves. At least partial dissolution of the latent binder helps to weaken the fragments 16' or granules 16, and forms a substantially continuous network of the soluble excipients.

The volume of the activation solvent 40 that is applied per unit of fragments 16' (or granules 16) in the patterned portion 44 may be sufficient to cause continuous network formation, which can lead to agglomeration of the plurality of excipient particles within the portion 44 of the layer 38 upon evaporation of the activation solvent 40.

When the active pharmaceutical ingredient formulation 42 is selectively applied in the desired portion(s) 44, the active pharmaceutical ingredient (present in the active pharmaceutical ingredient formulation 42) infiltrates the inter-particles spaces among the fragments 16' (or granules 16).

The volume of the active pharmaceutical ingredient formulation 42 that is applied per unit of fragments 16' (or granules 16) in the patterned portion 44 may be sufficient to achieve a desired dosage within the portion 44 of the layer 38.

It is to be understood that in some examples of the method 100, that active pharmaceutical ingredient formulation 42 may be applied in the same amount across the portion 44. In this example, the pharmaceutical tablet 48' that is formed contains the same dosage of the active pharmaceutical ingredient at least in the region corresponding with the portion 44.

It is to be understood that in some other examples of the method 100, that active pharmaceutical ingredient formulation 42 may be applied in different amounts at different areas of the at least the portion 44 of the pressed build material granules 16, 16'. The active pharmaceutical ingredient formulation 42 may be applied in different amounts at different areas of the portion 44 so that the active pharmaceutical ingredient is present in different amounts in the different areas, and so that the pharmaceutical tablet 48' that is formed contains different dosages of the active pharmaceutical ingredient in the areas corresponding to the different areas of the portion 44. For example, the active pharmaceutical ingredient formulation 42 may be applied so that a greater amount of the active pharmaceutical ingredient is present near the surface(s) and/or edges of the pharmaceutical tablet 48' to provide an initial burst of the active pharmaceutical ingredient.

In other examples, some area(s) of the portion 44 may have the activation solvent 40 applied thereto, but may not have the active pharmaceutical ingredient formulation 42 applied thereto. These area(s) of the portion 44 will become part of the pharmaceutical tablet 48' that is formed, but will not contain the active pharmaceutical ingredient. As such, these area(s) do not become part of the region of the pharmaceutical tablet 48' that contains the active pharmaceutical ingredient. Rather, these area(s) made up a placebo portion of the pharmaceutical tablet 48'

It is to be understood that in portions 46 of the build material fragments 16' that do not have the activation solvent 40 applied thereto, the latent binder of the fragments 16' does not dissolve, any soluble excipient particles in these portions 46 do not form a continuous network, and any insoluble excipient particles in these portions 46 do not agglomerate upon evaporation of the activation solvent 40.

As such, these portions 46 do not become part of the pharmaceutical tablet 48' that is ultimately formed. Since these portions 46 are not bound together by the activation solvent 40 to become part of the pharmaceutical tablet 48', these portions 46 also may not have the active pharmaceutical ingredient formulation 42 applied thereto.

In some examples, such as the example shown in FIG. 3E, the activation solvent 40 and the active pharmaceutical ingredient formulation 42 are applied in the same portion(s) (e.g., portion 44). In these examples, the region containing the active pharmaceutical ingredient is the entire layer of the pharmaceutical tablet 48'.

In other examples (not shown and briefly mentioned above), the method 100 may include applying the activation solvent 40 on a portion of the fragments 16' (or pressed granules 16) to which the active pharmaceutical ingredient formulation 42 is not applied. For example, the active pharmaceutical ingredient formulation 42 may be applied to a portion of the pressed build material granules 16 (and thus the portion is less than all of the pressed build material granules 16), and in this example, the activation solvent 40 may be selectively applied on another portion of the pressed build material granules 16, thereby dissolving the latent binder, and the evaporation of the activation solvent 40 causes agglomeration of the other portion of the pressed build material granules 16 and forms a remaining region of the layer of the pharmaceutical tablet 48'. In these examples, a region (i.e., the remaining region) that does not contain the active pharmaceutical ingredient is formed. The region without the active pharmaceutical ingredient may be an entire layer of the pharmaceutical tablet 48' or may be a remaining region of a layer that includes a region containing the active pharmaceutical ingredient (i.e., part of a layer is a placebo portion and another part of a layer contains active pharmaceutical ingredient). When the region without the active pharmaceutical ingredient is a remaining region of a layer that also includes the active pharmaceutical ingredient, the portion of the fragments 16' (or pressed granules) to which the active pharmaceutical ingredient formulation 42 is applied is less than all of the fragments 16' (or pressed granules). As an example, the method 100 may include applying the activation solvent 40 on all of the fragments 16' (or pressed granules) in a layer 38 and applying the active pharmaceutical ingredient formulation 42 to the center fragments 16' of the layer and not to the outer fragments 16' of the layer. This may create a layer of the pharmaceutical tablet that has a core that contains the active pharmaceutical ingredient and a shell that does not contain the active pharmaceutical ingredient.

It is to be understood that the activation solvent 40 may be selectively applied to pattern the layer 38, or multiple activation solvents 40 may be selectively applied to pattern the layer 38. When multiple activation solvents 40 are utilized, each is capable of at least partially dissolving the latent binder in the build material fragments 16' (or pressed granules 16). As an example, multiple activation solvents 40 may be used when one activation solvent 40 is included in the active pharmaceutical ingredient formulation 42, and another activation solvent 40 is applied on another portion of the fragments 16' (or pressed granules 16) to which the active pharmaceutical ingredient formulation 42 is not applied.

While not shown, in some examples, the method 100 may further include selectively applying another or second active pharmaceutical ingredient formulation including another or second active pharmaceutical ingredient on a portion of the pressed build material granules or fragments 16'. The other or second active pharmaceutical ingredient formulation may be used to introduce another or second active pharmaceutical ingredient, which may be different than the active pharmaceutical ingredient in the active pharmaceutical ingredient formulation 42, to the layer 38 and the final pharmaceutical tablet 48'.

The other or second active pharmaceutical ingredient formulation may be applied to the same portion(s) (e.g., portion 44) as, or different portion(s) than, the active pharmaceutical ingredient formulation 42 is applied. For example, the formulations may be applied to the same portion(s) when they are compatible (i.e., the active pharmaceutical ingredients in the formulations do not deleteriously react with or affect one another). As another example, the formulations may be applied to different portion(s) when they are not compatible (i.e., the active pharmaceutical ingredients in the formulations do deleteriously react with one another).

The other or second active pharmaceutical ingredient formulation may be applied to the fragments 16' (or pressed granules) with one of the applicators 28A, 28B (from a separate cartridge for dispensing the other or second active pharmaceutical ingredient formulation) or with a third applicator (not shown) that may be similar to the applicators 28A, 28B.

As shown at reference numeral 110 in FIG. 2, the method 100 continues by evaporating the activation solvent 40. It is to be understood that evaporation of the activation solvent 40 may be partial evaporation or complete evaporation. Evaporation of the activation solvent 40 may be partial evaporation when the presence of residual activation solvent 40 does not deleteriously affect the desired structural integrity of the pharmaceutical tablet 48'. The (partial or complete) evaporating of the activation solvent 40 causes agglomeration of the plurality of excipient particles in the at least the portion of the pressed build material granules 16 and forms a region of a layer of the pharmaceutical tablet 48', where the region contains the active pharmaceutical ingredient.

Evaporation of the activation solvent 40 may take place after a pharmaceutical tablet precursor 48 (see FIG. 3G) has been formed, or as each layer of the pharmaceutical tablet 48' is formed. Each of these examples will now be described.

The processes shown in FIGS. 3A through 3E may be repeated to iteratively build up several patterned layers and to form the pharmaceutical tablet precursor 48. As used herein, the term "pharmaceutical tablet precursor" refers to an intermediate tablet that has a shape representative of the final 3D printed tablet and that includes a continuous network of at least partially dissolved latent binder and any dissolved excipient component(s), activation solvent, and at least some active pharmaceutical ingredient in at least some of the layers. The pharmaceutical tablet precursor 48 has not been exposed to solvent evaporation (i.e., solvent is not evapoted in a layer-by-layer fashion) or to final extraction and pressing.

FIG. 3F illustrates the initial formation of a second layer of build material granules 16 on the layer 38 patterned with the activation solvent 40 and the active pharmaceutical ingredient formulation 42. In FIG. 3F, following deposition of the activation solvent 40 and the active pharmaceutical ingredient formulation 42 onto predetermined portion(s) 44 of the layer 38 of build material fragments 16', the controller 32 may execute instructions to cause the build area platform 12 to be moved a relatively small distance in the direction denoted by the arrow 20. In other words, the build area platform 12 may be lowered to enable the next layer of build material granules 16 to be formed. For example, the build material platform 12 may be lowered a distance that is equivalent to the height of the layer 38. In addition, following the lowering of the build area platform 12, the controller 32 may control the build material supply 14 to supply additional build material granules 16 (e.g., through operation of an elevator, an auger, or the like) and the build material distributor 18 to form another layer of build material granules 16 on top of the previously formed layer 38 with the additional build material granules 16. The newly formed layer may be exposed to applied pressure to crush the granules 16 and form fragments 16' (or to tighten the packing of the granules 16), and then the newly formed fragments 16' (or pressed granules 16) may be patterned with the activation solvent 40 and the active pharmaceutical ingredient formulation 42 (the latter of which is applied when it is desirable for at least part of the newly formed layer to include the active pharmaceutical ingredient).

Repeatedly forming, pressing, and patterning (or forming, patterning, and pressing) new layers results in the formation of a pressed cake 50, as shown in FIG. 3G, which includes the pharmaceutical tablet precursor 48 residing within the non-patterned portions 46 of each of the layers 38 of build material fragments 16'. As previously mentioned, the pharmaceutical tablet precursor 48 is a volume of the pressed cake 50 that is filled with the activation solvent 40, dissolved latent binder and any other soluble excipient(s) from the patterned fragments 16', and the active pharmaceutical ingredient (residing in fluid, which includes the remaining ingredients of the active pharmaceutical ingredient formulation 42). The remainder of the pressed cake 50 is made up of the non-patterned fragments 16'.

Also as shown in FIG. 3G, the pressed cake 50 may be exposed to heat or radiation to generate heat, as denoted by the arrows 52. The heat applied may be sufficient to evaporate the activation solvent 40 and/or the solvent of the active pharmaceutical ingredient formulation 42 from the pharmaceutical tablet precursor 48 and to produce the pharmaceutical tablet 48'. In one example, the heat source 36 may be used to apply the heat to the pressed cake 50. In the example shown in FIG. 3G, the pressed cake 50 may remain on the build area platform 12 while being heated by the heat source 36. Any of the previously described heat sources 36 may be used.

Referring back to FIG. 3E, in another example of the method 100, the layer 38 may be exposed to heating using heater 36 (e.g., integrated into the build material platform) or 36' after the activation solvent 40 and the active pharmaceutical ingredient formulation 42 are applied to the layer 38 and before another layer of build material granules 16 is formed thereon. The heater 36, 36' may be used to evaporate the activation solvent 40 and/or the solvent of the active pharmaceutical ingredient formulation 42 during printing layer-by-layer, and for producing a layer of the pharmaceutical tablet 48'. Heating and solvent evaporation in the layer-by-layer manner may facilitate rapid consolidation of the latent binder and other excipient particles that may be present, and may enable delivery of larger amounts of the active pharmaceutical ingredient into the printed excipient volume. The latter may be desirable when printing active pharmaceutical ingredients with low solubility in the liquid vehicle. On-going rapid evaporation of the liquid vehicle may prevent exceeding the absorbing capacity of the printed fragments 16'/granules 16 and thus enable printing active pharmaceutical ingredients at higher flux density in multiple print passes.

In a layer-by-layer example, the applying of the build material granules 16, the applying of pressure to the build material granules 16, the selectively applying of the activation solvent 40, the selectively applying of the active pharmaceutical ingredient formulation 42, and the evaporating of the activation solvent 40 are each accomplished on the build area platform 12. Then the method includes repeating the applying of the build material granules 16, the applying of pressure to the build material granules 16, the selectively applying of the activation solvent 40, the selectively applying of the active pharmaceutical ingredient formulation 42, and the evaporating of the activation solvent 40 to iteratively form multiple layers of the pharmaceutical tablet 48'. This example may also include printing tablet information on a top layer of the pharmaceutical tablet 48'; and extracting the pharmaceutical tablet 48' from the build area platform 12.

Heating to form the layer of the pharmaceutical tablet 48' may take place at a temperature that is capable of partially or completely evaporating the activation solvent 40 and/or the active pharmaceutical ingredient formulation 42. Examples of suitable evaporation temperatures are provided below. In this example, the processes shown in FIGS. 3A through 3E (including the heating of the layer 38) may be repeated to iteratively build up several layers and to ultimately produce the pharmaceutical tablet 48'. When the layers are heated separately, the layers are able to merge together due to the activation solvent 40 penetrating through the current layer to the underlying layer, which may redissolve the latent binder in the underlying layer and allow the current layer and the underlying layer to form an agglomeration upon the evaporation of the activation solvent 40.

Heating to form the pharmaceutical tablet 48' may take place at a temperature and for a time period that is capable of at least partially evaporating the activation solvent 40 and/or the solvent of the active pharmaceutical ingredient formulation 42. In an example, the evaporation temperature may be above ambient temperature. As used therein, "ambient temperature" may refer to room temperature (e.g., ranging about 18° C. to about 22° C.), or to the temperature of the environment in which the 3D printing method is performed. Examples of the 3D printing environment ambient temperature may range from about 40° C. to about 50° C. In an example, the evaporation temperature may be below the boiling point of the activation solvent 40 and/or the solvent of the active pharmaceutical ingredient formulation 42. In another example, the evaporation temperature is below a temperature at which the active pharmaceutical ingredient would be damaged (i.e., change its biologically active characteristic(s)). For a majority of activation solvents 40 and/or solvents of the active pharmaceutical ingredient formulation 42, the evaporation temperature ranges from about 10° C. to about 100° C. In an example, the evaporation temperature is about 50° C.

The evaporation time may depend, in part, on the evaporation temperature. For example, a higher evaporation temperature may result in a shorter evaporation time period, and a lower evaporation temperature result in a longer evaporation time period. Evaporation may vary, depending upon the temperature, humidity, and/or air circulation. For a majority of activation solvents 40 and/or solvents of the active pharmaceutical ingredient formulation 42, the evaporation time period ranges from about 1 second to about 1 minute per layer. In an example, the evaporation time period is about 30 seconds.

In some examples of the method 100, the activation solvent 40 and/or the solvent of the active pharmaceutical ingredient formulation 42 may be allowed to evaporate without heating. For example, more volatile solvents (e.g., acetone) can evaporate in seconds at room temperature. In these examples, pressed cake 50 or individual patterned layer is not exposed to heat or radiation to generate heat, and the activation solvent 40 and/or the solvent of the active pharmaceutical ingredient formulation 42 evaporates over time. In an example, the activation solvent 40 and/or the solvent of the active pharmaceutical ingredient formulation 42 may evaporate without heating within a time period ranging from about 1 second to about 1 minute.

At least partially evaporating (with or without heating) the activation solvent 40 and/or the solvent of the active pharmaceutical ingredient formulation 42 causes agglomeration of the excipient particles and forms the pharmaceutical tablet 48'. The evaporation of the activation solvent 40 and/or the solvent of the active pharmaceutical ingredient formulation 42 may also result in some densification, through capillary action, of the pharmaceutical tablet 48'.

Although the method 100 has been described with the layer of build material granules 16 being pressed prior to receiving the activation solvent 40 and the active pharmaceutical ingredient formulation 42, it is to be understood that the method 100 may additionally or alternatively include applying the activation solvent 40 and the active pharmaceutical ingredient formulation 42 onto the layer 38 of build material granules 16 (before being pressed and/or crushed) and then pressing the layer 38 with the pressing die 24 to form the fragments 16' (or pressed granules). In this example, the activation solvent 40 may soften the build material granules 16 by at least partially dissolving the latent binder therein.

While not shown, the method 100 may also include printing tablet information on a top layer of the pharmaceutical tablet 48'. The tablet information may include information identifying the active pharmaceutical ingredient, the total active pharmaceutical ingredient amount or dosage, tablet usage instructions, etc. The tablet information may be printed with the food grade colorant solution.

The food grade colorant solution may be applied to the top layer of the pharmaceutical tablet 48' with one of the applicators 28A, 28B (from a separate cartridge for dispensing the food grade colorant solution) or with a fourth applicator (not shown) that may be similar to the applicators 28A, 28B.

The pharmaceutical tablet 48' may be extracted from the pressed cake 50 or from surrounding non-patterned build material fragments 16'/granules 16. When used, the food grade colorant solution may be applied before or after extraction, depending, in part, upon which surface(s) of the tablet 48' are to receive the solution.

An example of the extraction process is shown in FIGS. 3H through 3K. Extraction may be accomplished with an extraction tool 54. The extraction tool 54 may include a piston 55 with a spring (not shown).

Figure 3H:
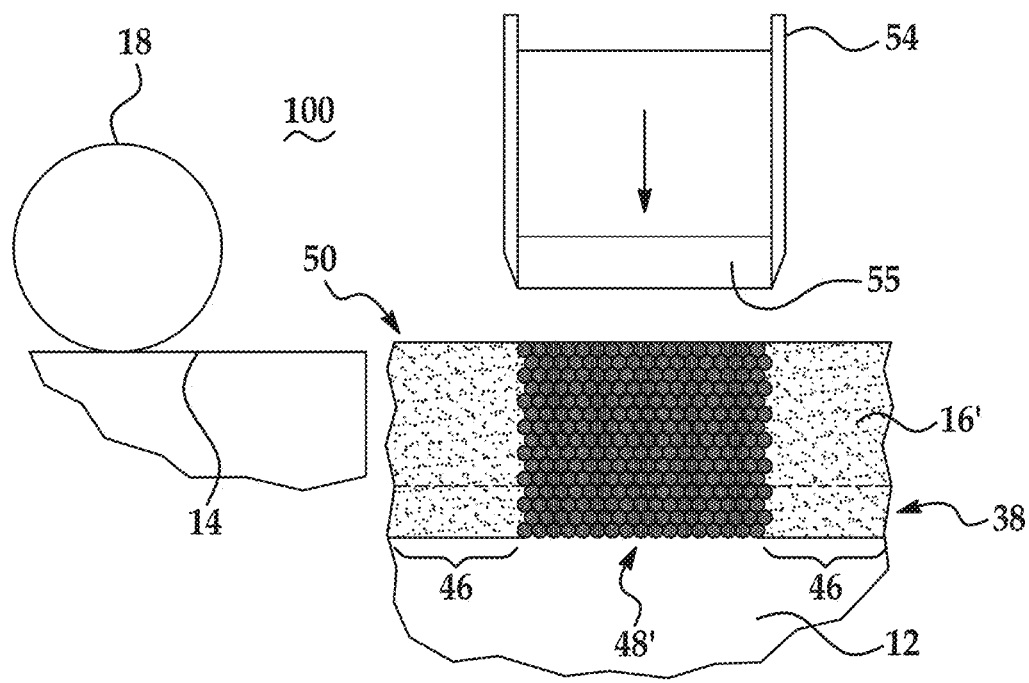
Figure 3I:
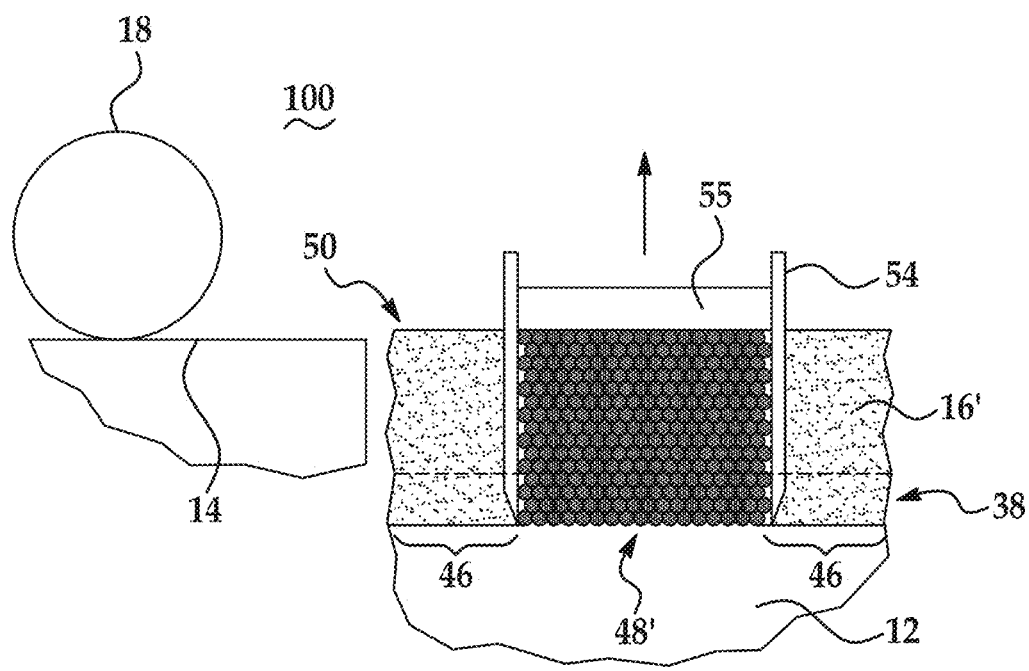
Figure 3J:
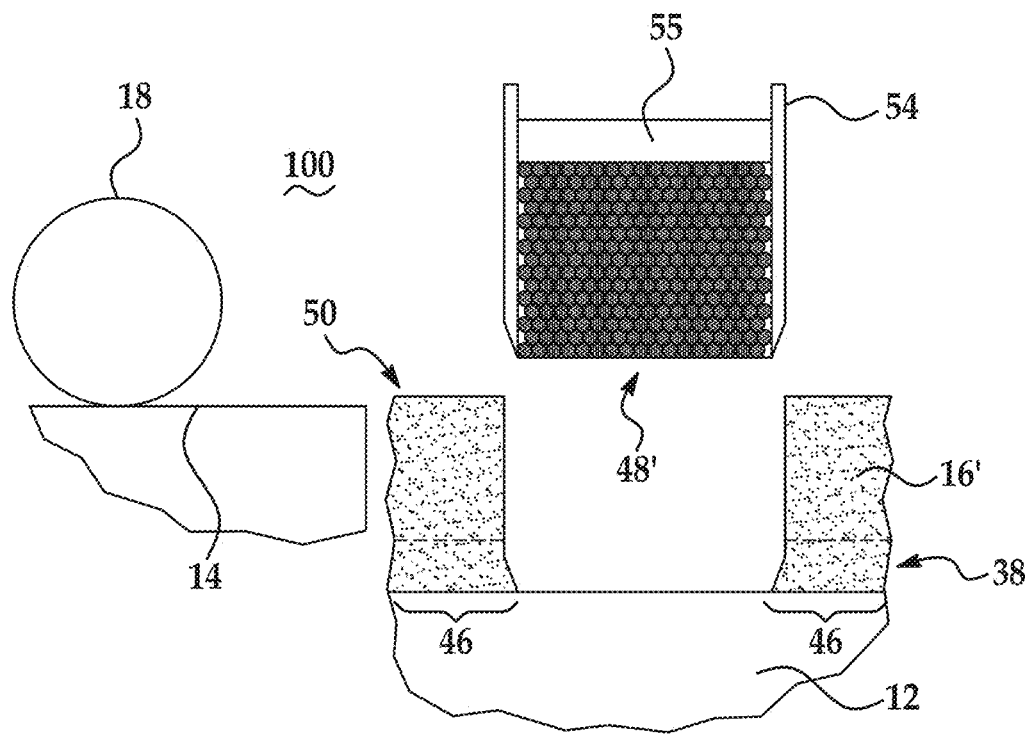
Figure 3K:
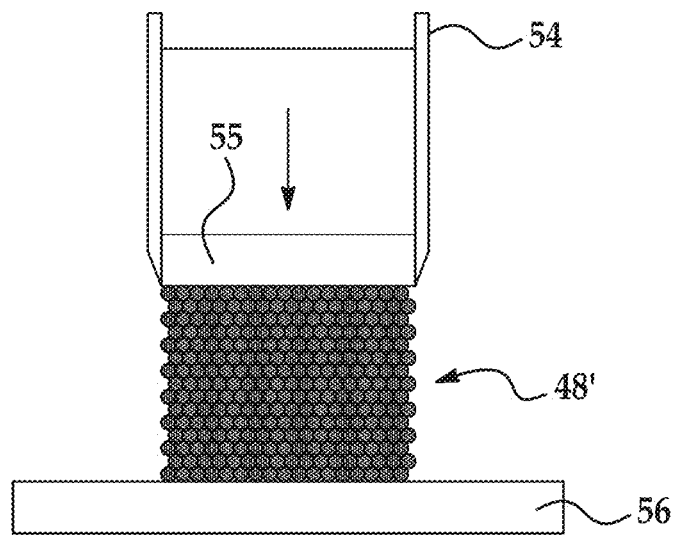

As shown in FIGS. 3H and 3I, the extraction tool 54 is pressed into the build material 16 adjacent to the sides or edges of the pharmaceutical tablet 48'. The piston 55 is pressed on top of the pharmaceutical tablet 48' as the tool 54 is driven toward the build material platform 12. This will prevent the pharmaceutical tablet 48' from mushrooming up. The positioned piston 55 becomes fixed to the extraction tool 54, e.g., with a latch or holder. Then the tool 54, pharmaceutical tablet 48', and piston 55 are lifted out together, as shown in FIG. 3J. The pharmaceutical tablet 48' is then ejected (e.g., onto a surface 56) by allowing the piston 55 to push it out from the inside of the extractor tool 54, as shown in FIG. 3K.

Although not shown, the operations depicted in FIGS. 3G through 3K may be automated and the controller 32 may control the operations.

The structure and porosity of the pharmaceutical tablet 48' may depend, at least in part, on the amount of latent binder in the build material granules 16, the flux density of the activation solvent 40 and the solvent of the active pharmaceutical ingredient formulation 42, and the amount of pressure applied to each layer of build material granules 16.

Additionally, in the examples disclosed herein, the amount and spatial distribution of the active pharmaceutical ingredient may be controlled throughout the pharmaceutical tablet 48', both in the x-y plane of each layer and in the z-direction. Inkjet printing of the active pharmaceutical ingredient formulation 42 enables this control. In an example, the outmost layer(s) of the pharmaceutical table 48' may have no active pharmaceutical ingredient added thereto, and the center or middle layer(s) of the pharmaceutical table 48' may have that highest amount of active pharmaceutical ingredient added thereto. Layers that are positioned between the outermost and middle layers may have a gradient of the active pharmaceutical ingredient increasing from the outermost layer(s) toward the middle layer(s). This example tablet 48' has a structure that facilitates time-variable (e.g., increased or ramped up) drug release rate over time.

To further illustrate the present disclosure, an example is given herein. It is to be understood that this example is provided for illustrative purposes and is not to be construed as limiting the scope of the present disclosure.

Example

Four tablets (referred to as "tablet 1," "tablet 2," "tablet 3," and "tablet 4") were printed. The build material used to print the tablets was a polyvinylpyrrolidone (PVP) powder having a molecular weight of about 10,000 Da (manufactured by Sigma-Aldrich). The particle size of the PVP powder, in terms of the volume-weighted mean diameter (MV) as measured on a Horiba LA950 particle size analyzer, was about 67 µm. A single activation/API formulation was used to print the tablets, and the single activation/API formulation contained water, glycerol, and Acid Blue dye. The Acid Blue dye was used as an active pharmaceutical ingredient proxy. The general formulation of the activation/API formulation used to print the tablets is shown in Table 2, with the wt % of each component that was used.

TABLE 2

| Component | Example activation/API formulation (wt %) |
|---|---|
| Glycerol | 10 |
| Acid Blue dye | 0.2 |
| Water | Balance |

The tablets were printed by applying a layer of the PVP powder, and then patterning the layer with the activation/API formulation. The layers of the PVP powder were not pressed for tablet 1 and tablet 2 before patterning, but the layers of PVP powder were pressed (under a pressure of about 30 psi) for tablets 3 and 4 before patterning. The activation/API formulation was jetted onto the PVP powder with a HP940 printhead cartridge (12 ng normal drop weight) at 33 gsm print flux density. Tablet 1 and tablet 3 were printed in the form of rectangles. Tablet 2 and tablet 4 were printed in the form of gears. After patterning each layer of the tablets with the activation/API formulation, the patterned surface was dried for 30 seconds at 50° C. via exposure to radiation from an infrared (IR) bulb. Ten stacked layers were printed, and the thickness of each layer was about 100 µm before pressing and pattering.

Figure 4A:
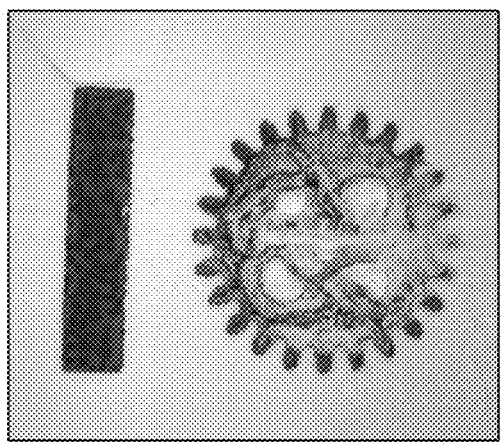
FIGS. 4A and 4B are black and white representations of originally colored photographic images of tablets after one layer was printed and after extraction from a powder bed.
Figure 4B:
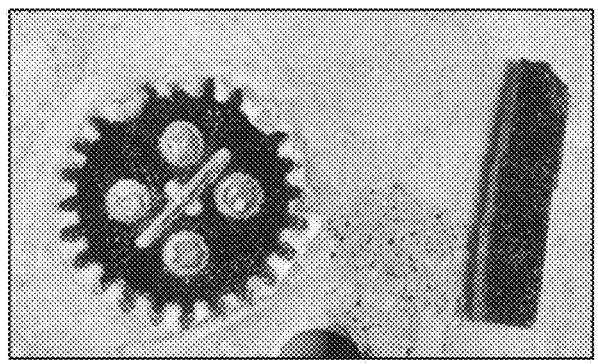

As previously mentioned, the layers of the PVP powder were not pressed for tablet 1 and tablet 2. FIG. 4A illustrates a first layer of tablet 1 (the rectangle on the left) and a first layer of tablet 2 (the gear on the right) after one layer was applied and patterned. As shown in FIG. 4A, the non-pressed PVP powder was shifted as a result of being wetted with the activation/API formulation. As such, the activation/API formulation disrupts the non-pressed patterned layers. FIG. 4B illustrates tablet 1 (the rectangle on the right) and tablet 2 (the gear on the left) after printing of the 10 layers was complete and after extraction from the powder bed.

Also as previously mentioned, the layers of the PVP powder were pressed with a pressure of about 30 psi before patterning for tablet 3 and tablet 4.

Figure 5A:
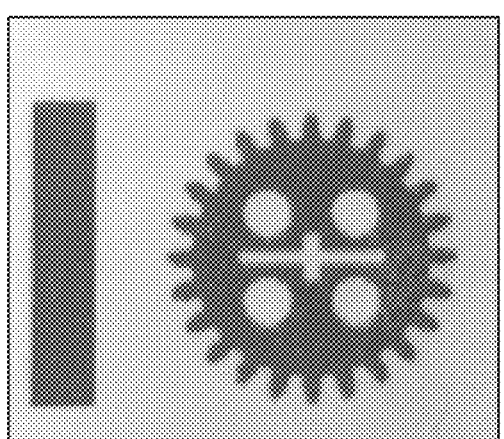
FIGS. 5A and 5B are black and white representations of originally colored photographic images of other tablets after one layer was printed and after extraction from the powder bed.
Figure 5B:
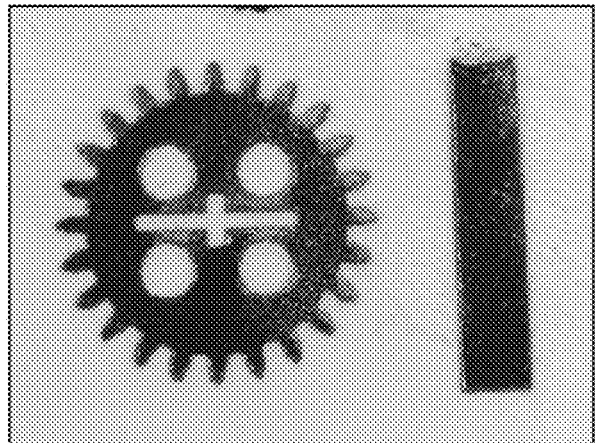

FIG. 5A illustrates a first layer of tablet 3 (the rectangle on the left) and a first layer of tablet 4 (the gear on the right) after one layer was applied, pressed, and patterned. As shown in FIG. 5A, application of pressure to the PVP powder prevented the shifting of the PVP powder upon application of the activation/API formulation, and the patterned layers were not disrupted. FIG. 5B illustrates tablet 3 (the rectangle on the right) and tablet 4 (the gear on the left) after printing of the 10 layers was complete and after extraction from the powder bed.

Each of the formed tablets had no visible porosity as the water-soluble PVP particles completely coalesced into bulk non-porous masses in the patterned areas. Each printed tablet was blue in color.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 20 µm to about 400 µm should be interpreted to include the explicitly recited limits of 20 µm to about 400 µm, as well as individual values, such as 25 µm, 77 µm, 125 µm, 200.5 µm, 230.55 µm, 395 µm, etc., and sub-ranges, such as from about 75 µm to about 275 µm, from about 30 µm to about 225 µm, from about 60 µm to about 325 µm, etc. Furthermore, when "about" is utilized to describe a value, this is meant to encompass minor variations (up to +/−10%) from the stated value.

In describing and claiming the examples disclosed herein, the singular forms "a", "an", and "the" include plural referents unless the context clearly dictates otherwise.

While several examples have been described in detail, it is to be understood that the disclosed examples may be modified. Therefore, the foregoing description is to be considered non-limiting.

What is claimed is:

1. A three-dimensional (3D) printing method for forming a pharmaceutical tablet, comprising:
    applying build material granules, each of the build material granules including a plurality of excipient particles, wherein at least one of the plurality of excipient particles is a latent binder;
    applying pressure to the build material granules, thereby forming a layer of pressed build material granules with microscopic porosity between the pressed build material granules;
    then selectively applying an activation solvent on at least a portion of the layer of the pressed build material granules;
    then selectively applying an active pharmaceutical ingredient formulation including an active pharmaceutical ingredient on the at least the portion of the layer of the pressed build material granules; and
    evaporating the activation solvent.

2. The method as defined in claim 1 wherein:
    the latent binder is at least partially soluble in the activation solvent; and
    the selectively applying of the activation solvent dissolves the latent binder.

3. The method as defined in claim 1 wherein the evaporating of the activation solvent causes agglomeration of the plurality of excipient particles in the at least the portion of the layer of the pressed build material granules and forms a region of a layer of the pharmaceutical tablet, the region containing the active pharmaceutical ingredient.

4. The method as defined in claim 3 wherein:
    the at least the portion of the layer of the pressed build material granules is less than all of the layer of the pressed build material granules;
    the method further comprises selectively applying the activation solvent on an other portion of the layer of the pressed build material granules, thereby dissolving the latent binder; and
    the evaporation of the activation solvent causes agglomeration of the other portion of the layer of the pressed build material granules and forms a remaining region of the layer of the pharmaceutical tablet.

5. The method as defined in claim 1 wherein the applying of the pressure to the build material granules forms crushed build material granules in the layer of the pressed build material granules.

6. The method as defined in claim 1, further comprising selectively applying an other active pharmaceutical ingredient formulation including an other active pharmaceutical ingredient on the at least the portion of the layer of the pressed build material granules.

7. The method as defined in claim 1 wherein the selectively applying of the active pharmaceutical ingredient formulation includes applying the active pharmaceutical ingredient formulation in different amounts at different areas of the at least the portion of the layer of the pressed build material granules.

8. The method as defined in claim 1 wherein:
    the applying of the build material granules, the applying of pressure to the build material granules, the selectively applying of the activation solvent, the selectively applying of the active pharmaceutical ingredient formulation, and the evaporating of the activation solvent are each accomplished on a build area platform; and
    the method further comprises:
        repeating the applying of the build material granules, the applying of pressure to the build material granules, the selectively applying of the activation solvent, the selectively applying of the active pharmaceutical ingredient formulation, and the evaporating of the activation solvent to iteratively form multiple layers of the pharmaceutical tablet;

printing tablet information on a top layer of the pharmaceutical tablet; and extracting the pharmaceutical tablet from the build area platform.

9. The method as defined in claim 1 wherein:

the latent binder is selected from a group consisting of povidone, polyethylene glycol (PEG), activation solvent soluble cellulose derivatives, activation solvent soluble starches, activation solvent soluble starch derivatives, activation solvent soluble proteins, sugars, sugar derivatives, sugar alcohols, and combinations thereof; and at least one other of the plurality of excipient particles includes:
- an insoluble bulk filler selected from a group consisting of microcrystalline cellulose, activation solvent insoluble polysaccharides, and combinations thereof;
- an additional component selected from a group consisting of an antiadherent, a disintegrant, a colorant, a flavoring agent, a preservative, and combinations thereof; or
- combinations thereof.

10. The method as defined in claim 1 wherein each of the plurality of excipient particles is the latent binder, and wherein the latent binder is selected from a group consisting of povidone, polyethylene glycol (PEG), activation solvent soluble cellulose derivatives, activation solvent soluble starches, activation solvent soluble starch derivatives, activation solvent soluble proteins, sugars, sugar derivatives, sugar alcohols, and combinations thereof.

11. The method as defined in claim 1 wherein prior to applying the build material granules, the method further comprises:

dissolving the latent binder, alone or in combination with a soluble excipient component, in an aqueous liquid;

dispersing an insoluble excipient component in the aqueous liquid; and spray drying or freeze spraying with subsequent freeze-drying the aqueous liquid containing the latent binder, the soluble excipient component, and the insoluble excipient component, thereby creating the build material granules.

12. The method as defined in claim 1 wherein the pressure applied to the build material granules ranges from about 20 psi to about 1,000 psi.

13. The method as defined in claim 1 wherein one of:

the activation solvent consists of water; or the activation solvent includes a monoglyceride, a diglyceride, lecithin, or a combination thereof.

14. The method as defined in claim 1 wherein the activation solvent and the active pharmaceutical ingredient formulation each exclude a binder.

* * * * *